US008628961B2

(12) United States Patent
Degterev et al.

(10) Patent No.: US 8,628,961 B2
(45) Date of Patent: Jan. 14, 2014

(54) SMALL MOLECULE ANTAGONISTS OF PHOSPHATIDYLINOSITOL-3,4,5-TRIPHOSPHATE (PIP3) AND USES THEREOF

(75) Inventors: Alexei Degterev, Brookline, MA (US); Chepuri Venkata Ramana, Pune (IN); Benchun Miao, Quincy, MA (US)

(73) Assignees: Tufts University, Boston, MA (US); Council of Scientific and Industrial Research, New Delhi (IN)

( * ) Notice: Subject to any disclaimer, the term of this patent is extended or adjusted under 35 U.S.C. 154(b) by 19 days.

(21) Appl. No.: 13/109,513

(22) Filed: May 17, 2011

(65) Prior Publication Data

US 2012/0016033 A1  Jan. 19, 2012

Related U.S. Application Data

(60) Provisional application No. 61/345,656, filed on May 18, 2010.

(51) Int. Cl.
*C12N 5/07* (2010.01)
*C12N 5/16* (2006.01)

(52) U.S. Cl.
USPC .......................................................... 435/375

(58) Field of Classification Search
USPC .......................................................... 435/375
See application file for complete search history.

(56) References Cited

U.S. PATENT DOCUMENTS 3,966,968 A * 6/1976 Andree et al. ................. 514/584

FOREIGN PATENT DOCUMENTS

WO  WO-2011/022028 A2  2/2011

OTHER PUBLICATIONS

Abe, K. et al., "The Complexity of TNF-Related Apoptosis-Inducing Ligand", *Ann. NY Acad. Sci.*, 926:52-63 (USA, 2000).
Adjei, A. et al., "Pulmonary Delivery of Peptide Drugs: Effect of Particle Size on Bioavailability of Leuprolide Acetate in Healthy Male Volunteers", *Pharm. Res.*, 7(6):565-569 (USA, 1990).
Auguin, D. et al., "Solution structure and backbone dynamics of the pleckstrin homology domain of the human protein kinase B (PKB/Akt). Interaction with inositol phosphates", *J. Biomol. NMR*, 28(2):137-155 (France, Feb. 2004.).
Avraamides, C. J., et al., "Integrins in angiogenesis and lymphangiogenesis", *Nat. Rev. Cancer*, 8(8):604-617 (USA, Aug. 2008).
Blume-Jensen, P. et al., "Oncogenic kinase signalling", *Nature*, 411(6835):355-365 (USA, May 17, 2001).
Cantley, L. C., "The Phosphoinositide 3-Kinase Pathway", *Science*, 296(5573):1655-1657 (USA, May 31, 2002).
Cardone, M. H. et al., "Regulation of Cell Death Protease Caspase-9 by Phosphorylation", *Science*, 282(5392):1318-1321 (USA, Nov. 13, 1998).
Castillo, S. S. et al., "Preferential Inhibition of Akt and Killing of Akt-Dependent Cancer Cells by Rationally Designed Phosphatidylinositol Ether Lipid Analogues", *Cancer Research*, 64:2782-2792 (USA, Apr. 15, 2004).
Cross, D. A. et al., "Inhibition of glycogen synthase kinase-3 by insulin mediated by protein kinase B", *Nature*, 378(6559): 785-789 (United Kingdom, Dec. 21-28, 1995).
Czech, M. P., "PIP2 and PIP3: Complex Roles at the Cell Surface", *Cell*,100:603-606 (USA, Mar. 17, 2000).
Datta, S. R. et al., "Akt Phosphorylation of BAD Couples Survival Signals to the Cell-Intrinsic Death Machinery", *Cell*, 91:231-241 (USA, Oct. 17, 1997).
Datta, S. R. et al., "Cellular survival: a play in three Akts", *Genes & Development*, 13:2905-2927 (USA, 1999).
Elstrom, R. L. et al., "Akt Stimulates Aerobic Glycosis in Cancer Cells", *Cancer Research*, 64:3892-3899 (USA, Jun. 1, 2004).
Etienne-Manneville, S. et al., "Rho GTPases in cell biology", *Nature*, 420(6916):629-635 (United Kingdom, Dec. 12, 2002).
Finnberg, N. et al., "TRAIL-R deficiency in mice promotes susceptibility to chronic inflammation and tumorigenesis", *Journ. Clin. Invest.*, 118(1):111-123 (USA, Jan. 2008).
Fruman, D. A. et al., "Phosphoinositide kinases", *Annu. Rev. Biochem.*, 67:481-507 (USA, 1998).
Fukata, M. et al., "Roles of Rho-family GTPases in cell polarization and directional migration", *Curr. Opin. Cell Biol.*, 15(5):590-597 (Japan, Oct. 2003).
Gao, Z. et al., "PEG-PE/phosphatidylcholine Mixed Immunomicelles Specifically Deliver Encapsulated Taxol to Tumor Cells of Different Origin and Promote Their Efficient Killing", *J. Drug Target.*, 11(2):87-92 (USA, Feb. 2003).
Gildea, J. J. et al., "PTEN can inhibit in vitro organotypic and in vivo orthotopic invasion of human bladder cancer cells even in the absence of its lipid phosphatase activity", *Oncogene*, 23:6788-6797 (Nature Publishing Group, USA, 2004).
Han, J. et al., "Role of Substrates and Products of PI 3-kinase in Regulating Activation of Rac-Related Guanosine Triphosphatases by Vav", *Science*, 279(5350):558-560 (USA, Jan. 23, 1998).
Hardie, D. G., "AMP-activated/SNF1 protein kinases: conserved guardians of cellular energy", *Nat. Rev. Mol. Cell Biol.*, 8(10);774-785 (United Kingdom, Oct. 2007).
Hornstein, I. et al., "Vav proteins, masters of the world of cytoskeleton organization", *Cell Signal*, 16(1):1-11 (Israel, Jan. 2004).

(Continued)

*Primary Examiner* — Shirley V Gembeh
(74) *Attorney, Agent, or Firm* — Alan W. Steele; Foley Hoag LLP

(57) ABSTRACT

Disclosed are new members of a class of non-lipid small molecule inhibitors which interfere with the interaction between phosphoinositol-3,4,5-triphosphate (PIP3) and pleckstrin homology (PH) domains. These molecules target a broad range of PIP3-dependent signaling events in vitro and exert significant anti-tumor activity in vivo, with improved activity and selectivity toward particular PH domains. The small molecule inhibitors of the invention can be used alone or together with tumor necrosis factor (TNF)-related apoptosis-inducing ligand (TRAIL) or other cancer medicament to treat cancer. Small molecule inhibitors of the invention act synergistically in combination with TRAIL and with other Akt inhibitors in treating cancer. Pharmaceutical compositions and methods for treating cancer are provided.

11 Claims, 6 Drawing Sheets

(56) References Cited

OTHER PUBLICATIONS

Hu, Y. et al., "3-(Hydroxymethyl)-Bearing Phosphatidylinositol Ether Lipid Analogues and Carbonate Surrogates Block PI3-K, Akt, and Cancer Cell Growth", *J. Med. Chem.*, 43(16):3045-3051 (USA, Aug. 10, 2000).

Kavran, J. M. et al., "Specificity and Promiscuity in Phosphoinositide Binding by Pleckstrin Homology Domains", *Journal of Biological Chemistry*, 273(46):30497-30508 (USA, Nov. 13, 1998).

Lemmon, M. A., "Membrane recognition by phospholipid-binding domains", *Nat. Rev. Mol. Cell Biol.*, 9(2):99-111 (USA, Feb. 2008).

Li, D.-M. et al., "PTEN/MMAC1/TEP1 suppresses the tumorigenicity and induces G1 cell cycle arrest in human glioblastoma cells", *Proc. Nat. Acad. Sci. USA*, 95:15406-15411 (National Academy of Sciences, USA, Dec. 1998).

Li, J. et al., "PTEN, a Putative Protein Tyrosine Phosphatase Gene Mutated in Human Brain, Breast, and Prostate Cancer", *Science*, 275(5308):1943-1947 (USA, Mar. 28, 1997).

Lopiccolo, J. et al., "Targeting Akt in cancer therapy", *Anticancer Drugs*, 18(8):861-874 (USA, Sep. 2007).

Maehama, T. et al., "PTEN: a tumour suppressor that functions as a phospholipid phosphatase", *Trends Cell Biol.*, 9(4):125-128 (USA, Apr. 1999).

Mahadevan, D. et al., "Discovery of a novel class of AKT pleckstrin homology domain inhibitors", *Mol. Cancer. Ther.*, 7(9):2621-2632 (USA, Sep. 2008).

Maroulakou, I. G. et al., "Akt1 Ablation Inhibits, whereas Akt2 Ablation Accelerates, the Development of Mammary Adenocarcinomas in Mouse Mammary Tumor Virus (MMTV)-ErbB2/Neu and MMTV-Polyoma Middle T Transgenic Mice", *Cancer Res.*, 67(1):167-177 (USA, Jan. 1, 2007).

Mathew, R., "Role of autophagy in cancer", *Nat. Rev. Cancer*, 7(12):961-967 (USA, Dec. 2007).

McManus, E. J. et al., "TSC1-TSC2: a complex tale of PKB-mediated S6K regulation", *Nat. Cell Biol.*, 4(9):E214-216 (Sep. 2002).

Meuillet, E. J. et al., "Specific Inhibition of the Akt1 Pleckstrin Homology Domain by D-3-Deoxy-Phosphatidyl-*myo*-Inositol Analogues", *Mol. Cancer. Ther.*, 2:389-399 (USA, Apr. 2003).

Nagane, M. et al., "The potential of TRAIL for cancer chemotherapy", *Apoptosis*, 6(3):191-197 (Japan, Jun. 2001).

Neshat, M. S. et al., "Enhanced sensitivity of PTEN-deficient tumors to inhibition of FRAP/mTOR", *PNAS*, 98(18):10314-10319 (Aug. 28, 2001).

Oikawa, T. et al., "PtdIns(3,4,5)$P_3$ binding is necessary for WAVE2-induced formation of lamellipodia", *Nat. Cell Biol.*, 6(5):420-426 (Japan, May 2004).

Oka, N. et al., "Galectin-3 Inhibits Tumor Necrosis Factor-Related Apoptosis-Inducing Ligand-Induced Apoptosis by Activating Akt in Human Bladder Carcinoma Cells", *Cancer Res.*, 65(17):7546-7553 (USA, Sep. 1, 2005).

Osaki, M. et al., "PI3K-Akt pathway: Its functions and alterations in human cancer", *Apoptosis*, 9(6):667-676 (Japan, Nov. 2004).

Peifer, C. et al., "Small-molecule inhibitors of PDK1", *ChemMedChem.*, 3(12):1810-1838 (United Kingdom, Dec. 2008).

Pore, N. et al., "PTEN Mutation and Epidermal Growth Factor Receptor Activation Regulate Vascular Endothelial Growth Factor (VEGF) mRNA Expression in Human Gioblastoma Cells by Transactivating the Proximal VEGF Promoter", *Cancer Res.*, 63:236-241 (USA, Jan. 1, 2003).

Powis, G. et al., "Wortmannin, a Potent and Selective Inhibitor of Phosphatidylinositol-3-kinase", *Cancer Res.*, 54(9):2419-2423 (USA, May 1994).

Puduvalli, V. K. et al., "TRAIL-induced apoptosis in gliomas is enhanced by Akt-inhibition and is independent of JNK activation", *Apoptosis*, 10(1):233-243 (USA, Jan. 2005).

Rameh, L. E. et al., "The Role of Phosphoinositide 3-Kinase Lipid Products in Cell Function", *Journal of Biological Chemistry*, 274(13):8347-8350 (USA, Mar. 26, 1999).

Ridley, A. J. et al., "The Small GTP-Binding Protein rac Regulates Growth Factor-Induced Membrane Ruffling", *Cell*, 70(3):401-410 (England, Aug. 7, 1992).

Salim, K. et al., "Distinct specificity in the recognition of phosphoinositides by the pleckstrin homology domains of dynamin and Bruton's tyrosine kinase", *EMBO Journal*, 15(22):6241-6250 (Oxford University Press, UK, 1996).

Santangelo, R. et al., "Efficacy of Oral Cochleate-Amphotericin B in a Mouse Model of Systemic Candidiasis", *Antimicrobial Agents and Chemotherapy*, 44(9):2356-2360 (USA, Sep. 2000).

Scheid, M. P. et al., "PKB/AKT: Functional Insights From Genetic Models", *Nat. Rev. Mol. Cell Biol.*, 2(10):760-768 (Canada, Oct. 2001).

Sheridan, J. P. et al., "Control of TRAIL-Induced Apoptosis by a Family of Signaling and Decoy Receptors", *Science*, 277(5327):818-821 (USA, Aug. 8, 1997).

Simpson, K. J. et al., "Functional Analysis of the Contribution of RhoA and RhoC GTPases to Invasive Breast Carcinoma", *Cancer Research*, 64:8694-8701 (USA, Dec. 1, 2004).

Stambolic, V. et al., "Functional distinctions of protein kinase B/Akt isoforms defined by their influence on cell migration", *Trends Cell Biol.*, 16(9):461-466 (Canada, Sep. 2006).

Takeuchi, H. et al., "Synergistic Augmentation of Rapamycin-Induced Autophagy in Malignant Glioma Cells by Phosphatidylinositol 3-Kinase/Protein Kinase B Inhibitors", *Cancer Res.*, 65(8):3356-3346 (USA, Apr. 15, 2005).

Tee, A. R. et al., "Tuberous sclerosis complex-1 and -2 gene products function together to inhibit mammalian target of rapamycin (mTOR)-mediated downstream signaling", *PNAS*, 99(21):13571-13576 (USA, Oct. 15, 2002).

Torchilin, V. P. et al., "Immunomicelles: Targeted pharmaceutical carriers for poorly soluble drugs", *PNAS*, 100(10):6039-6044 (USA, May 13, 2003).

Várnai, P. et al., "Phosphatidylinositol 3-Kinase-dependent Membrane Association of the Bruton's Tyrosine Kinase Pleckstrin Homology Domain Visualized in Single Living Cells", *Journal of Biological Chemistry*, 274(16):10983-10989 (USA, Apr. 16, 1999).

Venkateswarlu, K. et al., "Nerve growth factor- and epidermal growth factor-stimulated translocation of the ADP-ribosylation factor-exchange factor GRP1 to the plasman membrane of PC12 cells requires activation of phosphatidylinositol 3-kinase and the GRP1 pleckstrin homology domain", *Biochem. J.*, 335:139-146 (Great Britain, 1998).

Venkateswarlu, K. et al., "Signalling via ADP-ribosylation factor 6 lies downstream of phosphatidylinositide 3-kinase", *Biochem. J.*, 345:719-724 (Great Britain, 2000).

Vivanco, I. et al., "The Phosphatidylinositol 3-kinase Akt Pathway in Human Cancer", *Nat. Rev. Cancer*, 2(7):489-501 (USA, Jul. 2002).

Vlahos, C. J. et al., "A Specific Inhibitor of Phosphatidylinositol 3-Kinase, 2-(4-Morpholinyl)-8-phenyl-4H-1-benzopyran-4-one (LY294002)", *Journal of Biological Chemistry*, 269(7):5241-5248 (USA, Feb. 18, 1994).

Von Philipsborn, A. et al., "Mechanisms of Gradient Detection: A Comparison of Axon Pathfinding with Eukaryotic Cell Migration", *Int. Rev. Cytol.*, 263:1-62 (Germany, 2007).

Wang, F. et al., "Lipid products of PI(3)Ks maintain persistent cell polarity and directed motility in neutrophils", *Nat. Cell Biol.*, 4(7):513-518 (USA, Jul. 2002).

Wei, M. C. et al., "Proapoptotic BAX and BAK: A Requisite Gateway to Mitochondrial Dysfunction and Death", *Science*, 292(5517):727-730 (USA, Apr. 27, 2001).

Yaguchi, S. et al., "Antitumor Activity of ZSTK474, a New Phosphatidylinositol 3-Kinase Inhibitor", *Journal of the National Cancer Institute*, 98(8):545-556 (Japan, Apr. 19, 2006).

Yang, L. et al., "Akt/Protein Kinase B Signaling Inhibitor-2, a Selective Small Molecule Inhibitor of Akt Signaling with Antitumor Activity in Cancer Cells Overexpressing Akt", *Cancer Research*, 64:4394-4399 (USA, Jul. 1, 2004).

\* cited by examiner

SMALL MOLECULE ANTAGONISTS OF PHOSPHATIDYLINOSITOL-3,4,5-TRIPHOSPHATE (PIP3) AND USES THEREOF

RELATED APPLICATION

This application claims benefit under 35 U.S.C. 119(e) of U.S. Provisional Application No. 61/345,656, filed May 18, 2010.

BACKGROUND OF THE INVENTION

Dysregulation of the phosphoinositide 3-kinase (PI3K) pathway is implicated in many human diseases. Hyperactivation of this pathway contributes to human cancers, and defects in the pathway play a role in the development of type II diabetes. Therefore, key steps in this pathway represent promising targets for the development of drugs to combat these and other diseases associated with dysregulation of the PI3K pathway.

Class I PI3Ks (α, β and γ) are recruited to the plasma membrane in response to growth factor and hormone stimulation, where catalytic p110 subunits phosphorylate lipid phosphatidylinositol-4,5-bisphosphate (PIP2) at the D3 position to generate a second messenger phosphatidylinositol-3,4,5-trisphosphate (PIP3). Cantley L C (2002) *Science* 296: 1655-7. Conversely, the phosphatase PTEN specifically dephosphorylates the D3 position of PIP3 to produce PIP2. Loss of PTEN protein expression or function has been found in a large fraction of the advanced human cancers, indicating that uncontrolled signaling through PI3K contributes to tumorigenesis and metastasis. Maehama T et al. (1999) *Trends Cell Biol* 9:125-8. Furthermore, transgenic studies directly established that loss of PTEN leads to tumorigenesis. Li J et al. (1997) *Science* 275:1943-7; Vivanco I et al. (2002) *Nat Rev Cancer* 2:489-501.

PIP3 controls a complex cellular signaling network regulating cell growth, proliferation and cell survival, cytoskeletal rearrangements, and cell migration. PIP3 target proteins are located in the cytosol of unstimulated cells, but in response to lipid phosphorylation translocate to the plasma membrane because of their ability to associate with the newly formed PIP3 through its direct binding to pleckstrin-homology (PH) domains. Membrane translocation and, in some cases, activation of the PIP3 target factors initiate a variety of local responses, including polymerization of actin, assembly of signaling complexes, and priming of protein kinase cascades. Cantley L C (2002) *Science* 296:1655-7; Fruman D A et al. (1998) *Annu Rev Biochem* 67:481-507; Vivanco I et al. (2002) *Nat Rev Cancer* 2:489-501.

Among the PIP3-controlled signaling proteins, the serine-threonine Akt/PKB (Akt) protein kinase family is of particular interest, because it has been found to play a central role in wide range of fundamental cellular functions including cell survival, growth, and energy metabolism. Datta S R et al. (1999) *Genes Dev* 13:2905-27; Scheid M P et al. (2001) *Nat Rev Mol Cell Biol* 2:760-8. The mechanism by which Akt protects cells from death is likely to be multifactorial, involving direct phosphorylation of multiple components of the cell-death machinery such as FOXO transcription factors, BAD, glycogen synthase kinase-3 (GSK-3), and caspase-9. Akt also enhances protein synthesis and cell growth by activating mammalian target of rapamycin (mTOR), which, in concert with another PIP3-binding kinase, PDK1, stimulates p70 ribosomal protein S6 kinase (p70S6K) and inhibits translational repressor eukaryotic initiation factor 4E-binding protein 1 (4EBP1). Cardone M H et al. (1998) *Science* 282:1318-21; Cross D A et al. (1995) *Nature* 378:785-9; Datta S R et al. (1997) *Cell* 91:231-241; McManus E J et al. (2002) *Nat Cell Riot* 4:E214-216; Tee A R et al. (2002) *Proc Natl Acad Sci USA* 99:13571-6.

Other PH domain-containing proteins that are activated by PIP3 include general receptor for phosphoinositides-1 (GRP1, also known as cytohesin-3), GDP/GTP exchange factors (GEFs) for Rac, Rho and Cdc42 GTPases and ADP-ribosylating factor 6 (ARF6) and protein tyrosine kinases (PTKs) of the Bruton's tyrosine kinase (Btk) and Tec families. Venkateswarlu K et al. (1998) *Biochem J* 335:3139-46; Han J et al. (1998) *Science* 279:558-60; Salim K et al. (1996) *EMBO J* 15:6241-50; Venkateswarlu K et al. (2000) *Biochem J* 345 Pt 3:719-24. Activation of the Rac family or ARF6 by local gradients of PIP3 plays a major role in remodeling the actin cytoskeleton for directional motility in response to chemotactic agents and growth stimulation. These mechanisms play an important role in enhanced motility of cancer cells and cancer metastasis. Etienne-Manneville S et al. (2002) *Nature* 420:629-35; Hornstein I et al. (2004) *Cell Signal* 16:1-11; Venkateswarlu K et al. (2000) *Biochem J* 345 Pt 3:719-24.

Lipid-protein interactions play a key role in the downstream signaling in the PI3K pathway. Furthermore, this step is most commonly deregulated in cancer cells due to the loss of PTEN. However, until now, most of the therapeutic strategies targeting the PI3K pathway have focused on the development of inhibitors of PI3K, PDK1, or Akt kinase. Peifer C et al. (2008) *ChemMedChem* 3:1810-38; Powis G et al. (1994) *Cancer Res* 54:2419-23; Vlahos C J et al. (1994) *J Biol Chem* 269:5241-8; Yaguchi S et al. (2006) *J Natl Cancer Inst* 98:545-56; Yang L et al. (2004) *Cancer Res* 64:4394-9. Inhibitors of protein-protein interactions as cell biology tools and leads for drug development have attracted interest in recent years due to the recognition of the key role of such interactions in cellular signaling. Phospholipid-protein interactions, however, have not been as actively targeted, even though lipid molecules represent one of the most important classes of second messengers. This is surprising considering that they represent "prototypic" small molecule-protein interactions usually involving well defined binding sites. Lemmon M A (2008) *Nat Rev Mol Cell Biol* 9:99-111. Therefore, protein-lipid interactions may be more readily targetable by chemical inhibitors compared to protein-protein interactions, the latter frequently involving binding of the extended flat protein surfaces, thus presenting significant challenge for disruption by small molecules.

Degterev et al. recently identified a new class of non-lipid small molecule inhibitors targeting a broad range of PIP3-dependent signaling events in vitro and possessing significant anti-tumor activity in vivo. WO 2011/022028, filed May 17, 2010. This class of molecules includes compounds of Formula I

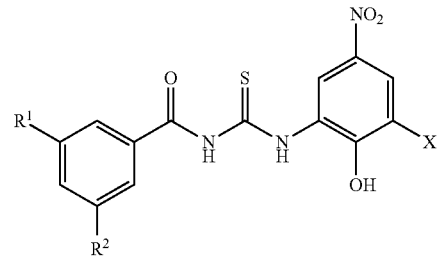

Formula I wherein X is selected from the group consisting of H and Cl, and each of $R^1$ and $R^2$ is independently selected from the group consisting of H and $CH_3$. These molecules were found to reduce binding of PIP3 to pleckstrin homology domain, thereby inhibiting PIP3-dependent cellular signaling pathways in a cell.

SUMMARY OF THE INVENTION

The instant invention concerns newly identified members of the class of non-lipid small molecule inhibitors targeting a broad range of PIP3-dependent signaling events in vitro and possessing significant anti-tumor activity in vivo. These molecules exhibit significantly improved activity and PH domain selectivity compared to those previously identified by Degterev et al. WO 2011/022028, filed May 17, 2010. Starting with a screen of a library of approximately 50,000 small molecules utilizing a PIP3/Akt PH domain binding assay, Degterev et al. previously identified the following compounds:

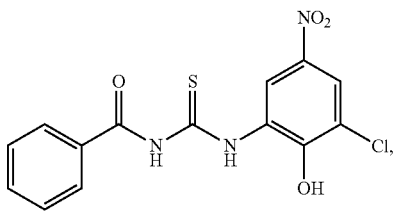 [SMILES: O=C(NC(=S)Nc1cc([N+](=O)[O-])cc(Cl)c1O)c1ccccc1]

termed PITenin-1 (PIT-1), and

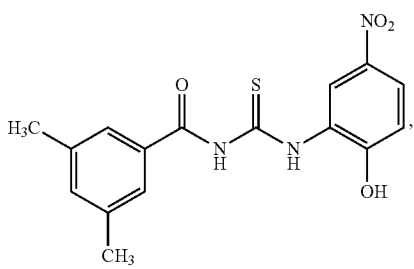 [SMILES: Cc1cc(C)cc(C(=O)NC(=S)Nc2cc([N+](=O)[O-])ccc2O)c1]

termed dimethyl PIT-1 (DM-PIT-1), as non-lipid small molecule antagonists of PIP3/PH interaction.

The instant inventors have now developed derivatives of PIT-1 with improved activity and PH domain selectivity compared to those previously identified by Degterev et al. WO 2011/022028, filed May 17, 2010. Similar to PIT-1 and DM-PIT-1, these improved compounds of the instant invention can be used to inhibit cancer cell survival, migration, and invasion, as well as angiogenesis, by specifically inhibiting PIP3-dependent signaling, resulting in a significant antitumor activity in vivo. In addition, however, some of the compounds of the instant invention can be used to achieve a greater selectivity toward particular PH domains, e.g., the various PH domains of Akt, PDK1, and GRP1.

An aspect of the invention is a method of selectively inhibiting a phosphoinositol-3,4,5-triphosphate (PIP3)-dependent cellular signaling pathway in a cell. The method includes the step of contacting a cell expressing PIP3 with an effective amount of a compound of Formula II

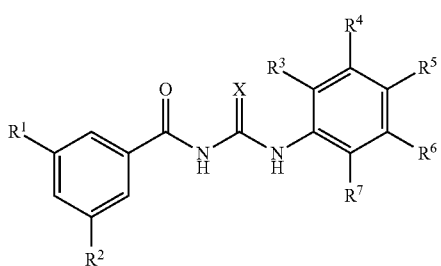

wherein
$R^1$ and $R^2$ are independently selected from H and —$CH_3$ (methyl),
$R^3$ and $R^5$ are independently selected from H, —$CH_3$ (methyl), and —$CF_3$,
$R^4$ is selected from H, —$CF_3$, phenyl, Cl, and Br,
$R^6$ is H,
$R^7$ is OH, and
X is S,
to reduce binding of PIP3 to pleckstrin homology domain, thereby selectively inhibiting the PIP3-dependent cellular signaling pathway in the cell.

An aspect of the invention is a method of treating cancer. The method includes the step of administering to a subject having a cancer an effective amount of a compound of Formula II

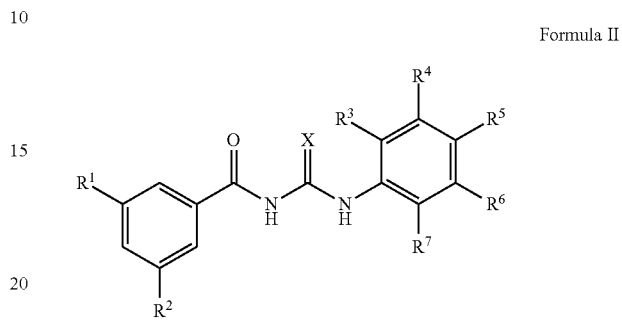

wherein
$R^1$ and $R^2$ are independently selected from H and —$CH_3$ (methyl),
$R^3$ and $R^5$ are independently selected from H, —$CH_3$ (methyl), and —$CF_3$,
$R^4$ is selected from H, —$CF_3$, phenyl, Cl, and Br,
$R^6$ is H,
$R^7$ is OH, and
X is S,
thereby treating the cancer.

An aspect of the invention is a pharmaceutical composition that includes a therapeutically effective amount of a compound of Formula II

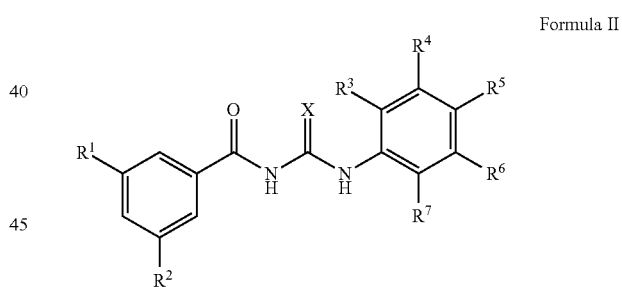

wherein
$R^1$ and $R^2$ are independently selected from H and —$CH_3$ (methyl),
$R^3$ and $R^5$ are independently selected from H, —$CH_3$ (methyl), and —$CF_3$,
$R^4$ is selected from H, —$CF_3$, phenyl, Cl, and Br,
$R^6$ is H,
$R^7$ is OH, and
X is S,
and a water-soluble delivery vehicle.

In one embodiment, the composition is formulated as nanoparticles.

In one embodiment, the nanoparticles comprise polyethylene glycol-phosphoethanolamine (PEG-PE) micelles.

In one embodiment, the water-soluble delivery vehicle comprises a targeting agent.

In each of the foregoing aspects of the invention, in one embodiment $R^4$ is phenyl.

In each of the foregoing aspects of the invention, in one embodiment $R^1$, $R^2$, $R^3$, and $R^5$ are each —$CH_3$ (methyl), and $R^4$ is selected from Cl and Br.

In each of the foregoing aspects of the invention, in one embodiment $R^1$ and $R^2$ are each —$CH_3$ (methyl), $R^3$ and $R^5$ are each H, and $R^4$ is —$CF_3$.

In each of the foregoing aspects of the invention, in one embodiment $R^1$ and $R^2$ are each —$CH_3$ (methyl), $R^3$ and $R^5$ are each —$CF_3$, and $R^4$ is H.

In each of the foregoing aspects of the invention, in one embodiment $R^1$ and $R^2$ are each —$CH_3$ (methyl), $R^3$ and $R^5$ are each H, and $R^4$ is phenyl.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

DETAILED DESCRIPTION OF THE INVENTION

Figure 1:
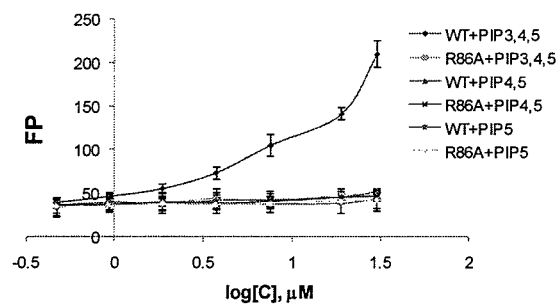
FIG. 1 is a graph depicting detection of the PIP3/PH domain binding using fluorescence polarization (FP) assay. Various concentrations of wild-type (WT) PH123 or mutant R86A were incubated with 15 nM TMR-labeled PIP3 (PIP3, 4,5), PIP2 (PIP4,5) or PIPS for 15 min, followed by FP measurement.

Because of the well established role of the over-activation of the PI3K pathway in human cancer, it is recognized as an attractive target for the therapeutic anti-cancer drug development. Blume-Jensen P et al. (2001) *Nature* 411:355-65; Osaki M et al. (2004) *Apoptosis* 9:667-76. Major emphasis, however, has been made on the inhibition of the enzymatic activities of PI3K and its downstream effector kinase, Akt. This effort has led to the development of multiple classes of the kinase inhibitors in vitro, which displayed promising activity in animal models. Powis G et al. (1994) *Cancer Res* 54:2419-23; Vlahos C J et al. (1994) *J Biol Chem* 269:5241-8; Yaguchi S et al. (2006) *J Natl Cancer Inst* 98:545-56; Yang L et al. (2004) *Cancer Res* 64:4394-9. The challenges for the development of these inhibitors are typical for kinase inhibitors, including potential off-target effects against other kinases, especially for ATP-competitive molecules. Another important consideration is the need to balance the efficacy of these molecules targeting multiple isoforms of the kinases versus potentially reduced efficacy of isoform-specific analogs of PI3K and Akt inhibitors. In addition, Akt inhibitors, in general, target just one, albeit very important, branch of the PIP3 network. It is also important to keep in mind that highly increased activity of oncogenic PI3K mutants or the lack of PIP3 degradation in PTEN-deficient cells may place strict requirements on the potency of such inhibitors.

Inhibitors of PIP3/protein binding present a very different approach to suppressing PI3K pathway. Low concentrations of PIP3 in cells and relatively low (micromolar) affinity of PIP3/PH domain interactions make development of PIP3 antagonists potentially promising. Czech M P et al. (2000) *Cell* 100:603-6; Rameh L E et al. (1999) *J Biol Chem* 274: 8347-50.

Previous efforts in developing PIP3 antagonists largely focused on phosphoinositide-like molecules. Several classes of such molecules have been reported to show promise in vitro and in vivo. Castillo S S et al. (2004) *Cancer Res* 64:2782-92; Hu Y et al. (2000) *J Med Chem* 43:3045-51. However, because these molecules lack phosphate groups (due to the lack of cell permeability by highly charged phosphorylated molecules), these analogs likely require phosphorylation by endogenous kinases in the cells. Hence, it may be difficult to achieve significant selectivity for PIP3 versus other phosphoinositides using this approach. Further modification is also required to increase their half-life in vivo considering the short half-life of endogenous PIPs.

Non-lipid small molecule antagonists have recently been shown to overcome these limitations. Degterev et al. WO 2011/022028. A family of small molecules, including a lead compound designated as NSC 348900 (4-[1-(4-chlorobenzoyl)-3-methyl-5-oxo-4,5-dihydro-1H-pyrazol-4-ylazo]-N-pyrimidine-2-yl-benzenesulfonamide), capable of interacting with PH domains of Akt, PDK1, and IRS1 has been recently described, although competition with PIP3 binding has not been characterized and the molecules lacked in vivo anti-tumor activity. Mahadevan et al. (2008) *Mol Cancer Ther* 7:2621-32. These compounds were identified by in silico library screening for molecules that bind selectively to the PH domain of Akt1.

Figure 2:
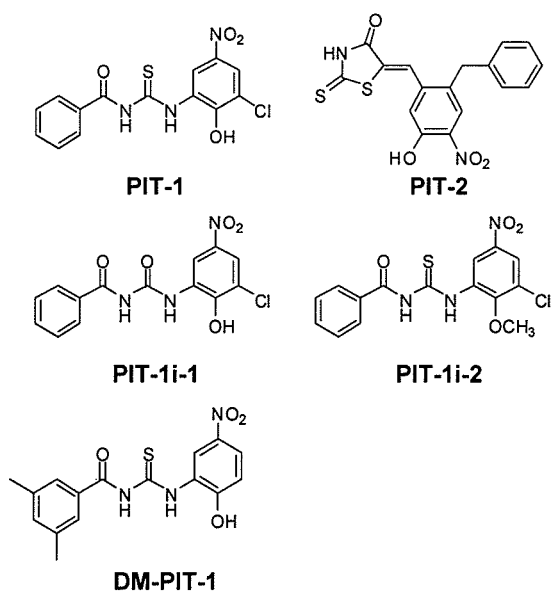
FIG. 2 depicts structures of PIT-1, PIT-2, DM-PIT-1 and inactive derivatives of PIT-1, PIT-1i-1 and PIT-1i-2.
Figure 4:
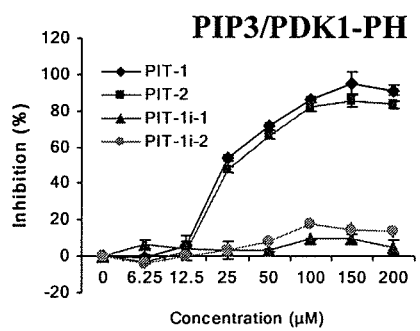
FIG. 4 is a graph depicting concentration-dependent competitive inhibition of PIP3-PH domain interaction by PIT-1 and PIT-2. 15 nM TMR-conjugated PIP3 were incubated with 100 nM PDK1 PH domain in the presence or absence of the indicated concentrations of PITs (0-200 μM) for 30 min, followed by FP measurement.

As described in the examples below, screen of ~50,000 diverse small molecules resulted in the selection of two distinct inhibitors of PIP3/PH domain binding, which were termed PIT-1 and PIT-2 (FIG. 2). These small molecules disrupted PIP3/Akt PH domain binding with $IC_{50}$=28.14 µM for PIT-1 and 31.52 µM for PIT-2. Analysis of several analogs of PIT-1 suggested that thiourea and hydroxyl groups are important for activity in vitro. The same analysis also provided closely related inactive analogs of PIT-1, termed PIT-1i-1 and PIT-1i-2 (FIG. 2). Also as described in the examples below, further characterization of these compounds indicate that PIT-1 and PIT-2 are selective non-phosphoinositide-related antagonists of PIP3/PH domain binding. Similar to the Akt PH domain, PIT-1 and PIT-2 inhibited binding of PIP3 to the PH domain of PDK1 (FIG. 4). In contrast to the PIP3-specific Akt and PDK1 PH domains, however, PIT-1 and PIT-2 failed to inhibit the interaction between PIP2 and PH domain of PLC-δ, which is known to have a preference for this lipid. Czech M P et al. (2000) *Cell* 100:603-6; Rameh L E et al. (1999) *J Biol Chem* 274:8347-50.

Furthermore, in contrast to the non-lipid small molecule antagonists such as NSC 348900, the non-lipid small molecule PIP3 antagonists (PITs) of the instant invention are specific for PIP3, i.e., they specifically inhibit interaction between PIP3 and pleckstrin homology domain, thereby specifically inhibiting recruitment of PIP3-binding proteins to the plasma membrane and suppressing growth factor-induced PIP3-dependent cellular signaling pathways.

Despite the specificity of the non-lipid small molecule PIP3 antagonists of Degterev et al. (supra) for PIP3 binding domains (compared to those recognizing PIP2), similar selectivity in distinguishing different PIP3-specific PH domains was not observed. Notably, even though PITs were selected in an Akt PH domain binding assay, they displayed higher activity in inhibiting cell migration and invasion, compared to the induction of cell death, which is likely mediated through inhibition of the targets other than Akt. These results may be understood considering similar structural basis for PIP3 binding to PH domains (Kavran J M et al. (1998) *J Biol Chem* 273:30497-508) and micromolar affinity of PITs towards PH domains. This likely implies that cellular activities of previously identified PITs are not linked to inhibition of a single protein target, but rather to a range of PIP3 targets. Indeed, as described herein, previously identified PITs inhibit multiple PIP3-dependent signaling events. This may contribute to the multimodal activity displayed by PITs in vitro and substantial anti-cancer activity displayed by relatively low doses of DM-PIT-1 in vivo.

Inhibition of the PIP3/protein binding represents a powerful, yet relatively unexplored approach to alter PI3K signaling, as PIP3/PH domain binding is a universal upstream step in the PI3K signaling pathway. Examples of PIP3 antagonists, utilizing lipid scaffolds, primarily alkylphospholipids and phosphatidylinositol ether lipid analogs (PIAs) have been described. These molecules interact with the Akt PH domain and block Akt membrane translocation and activation. However, achieving selectivity towards specific phosphoinositide targets is likely to be difficult with such scaffolds. PIA molecules, for example, utilize a modified non-phosphorylated inositol headgroup. Thus, it may be reasonable to expect that cellular activities of PIAs would require phosphorylation by endogenous lipid kinases. It may be very challenging to achieve selectivity of PIAs for a specific phosphoinositide, e.g., PIP3, versus other phosphoinositides as well as within the subfamily of PIP3-binding PH domains. At present, the selectivity profile of these molecules has not been established and Akt PH domain remains their only known PIP3-dependent target. Non-phospholipid/nonphosphoinositide small molecule antagonists present a good alternative starting point for the selective modulation of the PI3K signaling network. PITs represent the first class of directly competitive and selective non-phosphoinositide small molecule antagonists of PIP3 in vitro, in the cells and in vivo. PIT inhibitors were developed based on their ability to antagonize PIP3 binding to the PH domain of Akt. Akt is recognized as an important therapeutic target downstream from PI3K. Both direct ATP-competitive inhibitors of Akt and allosteric inhibitors, targeting the interface between the PH domain and the Akt kinase domain have been developed. LoPiccolo J et al. (2007) *Anticancer Drugs* 18:861-874. The instant invention concerns a different approach to inhibition of cellular Akt signaling, targeting membrane localization and activation of the kinase. Because of a different mode of action, these inhibitors can be combined with existing Akt kinase inhibitors to achieve greater efficacy in blocking Akt signaling, thereby opening avenues for Akt-directed combination therapy. Moreover, the different mode of action of PITs may offer benefits in blocking PIP3 signaling when combined with existing PI3K inhibitors. Importantly, efficient suppression of PIP3 signaling by PI3K inhibitors is negatively influenced by the loss of the PIP3 phosphatase PTEN, hydrolyzing pre-existing pool of PIP3. PTEN is frequently inactivated in tumor cells, e.g., many glioblastomas, breast, endometrium and colon cancers. Thus, combining PI3K inhibitors with PITs, acting downstream from the PTEN-dependent step, may represent a promising strategy, especially against PTEN deficient tumors. Furthermore, cells deficient in PTEN, which are adapted to growth in the presence of high PIP3 levels, display increased sensitivity to killing by PITs, compared to matched cells expressing functional PTEN.

One of the important future directions of anti-cancer drug discovery is the targeting of specific branches of the PI3K pathway, which would limit side effects of global PI3K pathway inhibition. PIP3 binding is a common mechanism controlling all branches of the PI3K-dependent signaling network. To this end, it is here shown that chemical modification of PIT-1 results in profound changes in the selectivity profile of the molecule. Combining extensive data profiling PIP3/PH domain binding with further chemical modification of PIT-1 or molecules with a similar mode of action may represent a promising approach to developing useful tool compounds for dissecting cellular PIP3 signaling network. Furthermore, PIT compounds, possessing different mode of action profiles, could also be attractive as leads for anti-cancer drug discovery.

While a known Akt inhibitor displayed activity similar to that of PITs in cell death assays, it was ineffective in attenuating cell migration, consistent with the role of a different class of PIP3 targets (i.e., Rho GEFs and WAVEs) in this process. Hornstein I et al. (2004) *Cell Signal* 16:1-11; Oikawa T et al. (2004) *Nat Cell Biol* 6:420-6. As disclosed herein, this class of targets is also inhibited by PITs, explaining the efficient suppression by PITs of both cell survival and cancer cell migration.

At the same time, while broad selectivity towards PIP3/PH binding may offer functional benefits against cancer cells, identification of PITs also offers new chemical scaffolds to generate target-specific PIT derivatives either through combinatorial chemistry or structure-based drug design, providing means to selectively manipulate specific aspects of the PIP3 network. Structure-based development of PITs may prove particularly feasible due to the extensive structural data available for multiple PIP3/PH domain complexes.

The invention concerns molecules structurally and functionally related to PIT-1. Such molecules are disclosed as "analogs" and "derivatives" of PIT-1. As used herein, the terms "analog" and "derivative" are used interchangeably.

Compounds of the invention are compounds of Formula II

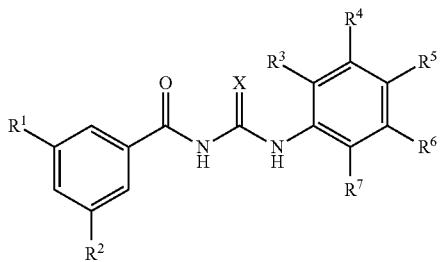

Formula II wherein
  $R^1$ and $R^2$ are independently selected from H and C1-C5 alkyl,
  $R^3$ and $R^5$ are independently selected from H, C1-C5 alkyl, and $—CF_3$,
  $R^4$ is selected from H, $—CF_3$, C1-C12 alkyl, substituted or unsubstituted phenyl, $NO_2$, and halide,
  $R^6$ is H,
  $R^7$ is OH, and
  X is O or S, proviso such molecule is not PIT-1, DM-PIT-1, PIT-1i-1, or PIT-1i-2.

In one embodiment, X is S.
In one embodiment, $R^4$ is substituted or unsubstituted phenyl. In one embodiment, $R^4$ is unsubstituted phenyl (i.e., $R^4$ is phenyl).
In one embodiment, $R^1$ and $R^2$ are independently selected from H and $—CH_3$ (methyl), $R^3$ and $R^5$ are independently selected from H, $—CH_3$ (methyl), and $—CF_3$, $R^4$ is selected from H, $—CF_3$, phenyl, Cl, and Br, $R^6$ is H, $R^7$ is OH, and X is S.
In one embodiment (PIT-3), each of $R^1$, $R^2$, $R^3$, and $R^5$ is $—CH_3$ (methyl), $R^4$ is Cl, $R^6$ is H, $R^7$ is OH, and X is S.
In one embodiment (PIT-4), each of $R^1$ and $R^2$ is $—CH_3$ (methyl), each of $R^3$ and $R^5$ is H, $R^4$ is $—CF_3$, $R^6$ is H, $R^7$ is OH, and X is S.
In one embodiment (PIT-5), each of $R^1$ and $R^2$ is $—CH_3$ (methyl), each of $R^3$ and $R^5$ is $—CF_3$, $R^4$ is H, $R^6$ is H, $R^7$ is OH, and X is S.
In one embodiment (PIT-6), each of $R^1$, $R^2$, $R^3$, and $R^5$ is $—CH_3$ (methyl), $R^4$ is Br, $R^6$ is H, $R^7$ is OH, and X is S.
In one embodiment (PIT-7), each of $R^1$ and $R^2$ is $—CH_3$ (methyl), each of $R^3$ and $R^5$ is H, $R^4$ is phenyl, $R^6$ is H, $R^7$ is OH, and X is S.

As used herein, "PIP3-mediated signaling" refers to any PIP3-mediated intracellular event involving or following an interaction between PIP3 and a polypeptide that includes a pleckstrin homology domain. In this context, "following an interaction between PIP3 and a polypeptide that includes a pleckstrin homology domain" refers to any one or more events or steps downstream of PIP3 in the well known PI3K pathway. PIP3-mediated signaling thus includes such phenomena as the recruitment of any PIP3 target protein to the plasma membrane, binding of PIP3 to PH domains, polymerization of actin, assembly of signaling complexes, priming of protein kinase cascades. PIP3 target proteins are polypeptides and proteins that include at least one PH domain, and such molecules include, without limitation, Akt, GRP1, GDP/GTP exchange factors (GEFs) for Rac, Rho, and Cdc42 GTPases and ADP-ribosylating factor 6 (ARF6), and protein tyrosine kinases of the Bruton's tyrosine kinase (Btk) and Tec families. In one embodiment PIP3-mediated signaling specifically includes phosphorylation (activation) of Akt. In one embodiment PIP3-mediated signaling specifically refers to phosphorylation (activation) of Akt.

A pleckstrin homology (PH) domain is a ca. 100 to 120-amino acid modular fold found, for example, in over 250 human proteins. PH domains have few critically conserved amino acids but show remarkable conservation of three-dimensional structure. Crystal structures and nuclear magnetic resonance structures of several PH domains show a highly conserved three-dimensional organization, although sequence identities are only 7% to 23%. The core of each PH domain consists of a β-barrel of seven antiparallel β-strands and a COOH-terminal amphipathic α-helix. PH domains can bind to Gβγ subunits of heterotrimeric G proteins, to certain phosphotyrosine peptides, polyproline sequences, and phosphoinositides (PtdIns). A majority of PH domain members bind PtdIns weakly and nonspecifically, but a subclass of approximately 40 PH domain proteins shows high affinity for phosphoinositides. These PtdIns-binding PH domain proteins are important components of signal transduction pathways that regulate cancer cell growth and survival.

PtdIns-binding PH domains can be classified according to their binding specificity based on conserved positively charged residues in the phosphatidylinositol phosphate binding pocket and have $K_D$s in the range of 1 to 5 µmol/L. Group 1 PH domains specifically recognize PtdIns(3,4,5)P$_3$ (PIP3). Group 2 PH domains bind PtdIns(4,5)P$_2$ (PIP2) and also interact with other phosphoinositides, but because PIP2 is more abundant than 3-phosphorylated phosphoinositides, PH domains in group 2 are regulated by PIP2. Group 3 PH domains recognize PIP2 and PIP3. Group 4 PH domains have a low affinity for PtdIns binding. Group 2 PH domains mediate the effects of PIP2 on membrane trafficking and plasma membrane-cytoskeleton linkages, whereas group 1 and group 3 PH domains mediate the effects of PIP3 on cell signaling pathways that regulate growth and survival. Akt has a group 3 PH domain.

As used herein, "selectively inhibiting" in connection with cell signaling refers to inhibiting one particular type of cell signaling largely to the exclusion of inhibiting any unrelated type of cell signaling. In one embodiment, selectively inhibiting refers to inhibiting one particular type of cell signaling essentially to the exclusion of inhibiting any unrelated type of cell signaling. In one embodiment, selectively inhibiting refers to inhibiting one particular type of cell signaling at least 10 times more effectively than inhibiting any unrelated type of cell signaling. In one embodiment, selectively inhibiting refers to inhibiting one particular type of cell signaling at least 20 times more effectively than inhibiting any unrelated type of cell signaling. In one embodiment, selectively inhibiting refers to inhibiting one particular type of cell signaling at least 50 times more effectively than inhibiting any unrelated type of cell signaling. In one embodiment, selectively inhibiting refers to inhibiting one particular type of cell signaling at least 100 times more effectively than inhibiting any unrelated type of cell signaling.

As used herein, an "antagonist of binding" refers to a molecule that is capable of interfering with the noncovalent binding interaction between a first molecule and a second molecule, such that the noncovalent binding interaction is reduced by at least 50% from control. In various embodiments the noncovalent binding interaction is reduced by at least 50%, at least 60%, at least 70%, at least 80%, at least 90%, at least 95%, and at least 99%. An antagonist of binding of PH domain to PIP3 thus refers to a molecule that is capable of interfering with the noncovalent binding interaction between PH and PIP3, such that the noncovalent binding interaction is reduced by at least 50% from control. In individual embodiments the noncovalent binding interaction between PH and PIP3 is reduced by at least 50%, at least 60%, at least 70%, at least 80%, at least 90%, at least 95%, and at least 99%.

The method involves use of a PIP3-specific non-phosphoinositide small molecule antagonist of binding of PH domain to PIP3. As used herein, "PIP3-specific" means that the antagonist is capable of inhibiting interaction between PH and PIP3, largely without inhibiting interaction between PH and other phosphatidylinositol phosphate molecules, including, in particular, PIP2. In one embodiment "PIP3-specific" means that the antagonist is capable of inhibiting interaction between PH and PIP3, essentially to the exclusion of inhibiting interaction between PH and other phosphatidylinositol phosphate molecules, including, in particular, PIP2. In one embodiment "PIP3-specific" means that the antagonist is capable of inhibiting interaction between PH and PIP3, with no more than 10% inhibiting of interaction between PH and other phosphatidylinositol phosphate molecules, including, in particular, PIP2, under similar conditions. In one embodiment "PIP3-specific" means that the antagonist is capable of inhibiting interaction between PH and PIP3, with no more than 5% inhibiting of interaction between PH and other phosphatidylinositol phosphate molecules, including, in particular, PIP2, under similar conditions. In one embodiment "PIP3-specific" means that the antagonist is capable of inhibiting interaction between PH and PIP3, with no more than 1% inhibiting of interaction between PH and other phosphatidylinositol phosphate molecules, including, in particular, PIP2, under similar conditions.

As used herein, a "non-phosphoinositide small molecule", and equivalently a "non-lipid small molecule", refers to an organic molecule, other than a phosphoinositide or lipid-based molecule, having a molecular weight of less than or equal to 1500 Daltons. This term is understood specifically to exclude D-3-deoxy-phosphatidylinositol ether lipid (DPIEL, PX-316) (Meuillet E J et al. (2003) *Mol Cancer Ther* 2:389-99), phosphatidylinositol ether lipid analogs (see, e.g., Castillo S S et al. (2004) *Cancer Res* 64:2782-92), as well as NSC 348900 and analogs thereof disclosed in Mahadevan D et al. (2008) *Mol Cancer Ther* 7:2621-32.

In one embodiment a non-phosphoinositide small molecule antagonist of binding of pleckstrin homology domain to PIP3 is a thiourea-containing compound, examples of which include, without limitation, PIT-1 and DM-PIT-1.

A cell expressing PIP3 is contacted with an effective amount of a PIP3-specific non-phosphoinositide small molecule antagonist of binding of pleckstrin homology domain to PIP3, thereby selectively inhibiting PIP3-mediated signaling in the cell. As used herein, a "cell expressing PIP3" refers to any cell that expresses a detectable amount of PIP3. In one embodiment the cell is a mammalian cell that naturally expresses PIP3. In one embodiment the cell is a human cell that naturally expresses PIP3. In one embodiment the cell is a cancer cell, including, without limitation, a cell that is part of or isolated from a tumor spontaneously arising in a human or other mammal. In one embodiment the cell is a cancer cell that is part of or isolated from a tumor cell line. PIP3 expression can be detected using any suitable method, for example, enzyme-linked immunosorbent assay (ELISA), fluorescence-activated cell sorting (FACS), fluorescent microscopy, or fluorescence polarization, using suitable antibodies specific for PIP3 in accordance with standard methods.

As used herein, "contacted" refers to any situation in which two or more materials, such as a cell and a compound in accordance with the invention, are brought into intimate physical contact with one another.

As used herein, the phrase "effective amount" refers to any amount that is sufficient to achieve a desired biological effect. Thus, for example, an effective amount for selectively inhibiting PIP3-mediated signaling in a cell is an amount that is sufficient to cause selective inhibition of PIP3-mediated signaling in the cell. In one embodiment an effective amount is also an amount that is not generally toxic to a cell, or to a population of cells, under physiological conditions.

The invention in one aspect is a method of selectively inhibiting a PIP3-dependent cellular signaling pathway in a cell. The method includes the step of contacting a cell expressing PIP3 with an effective amount of a compound of Formula II

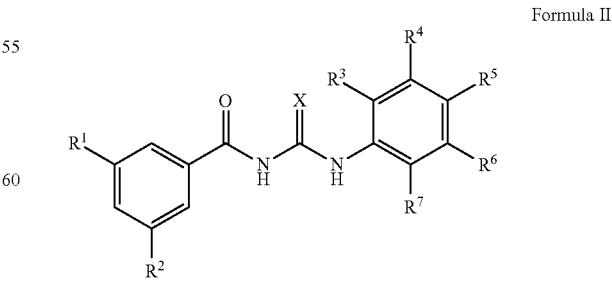

Formula II wherein
R$^1$ and R$^2$ are independently selected from H and C1-C5 alkyl, $R^3$ and $R^5$ are independently selected from H, C1-C5 alkyl, and —$CF_3$, $R^4$ is selected from H, —$CF_3$, C1-C12 alkyl, substituted or unsubstituted phenyl, $NO_2$, and halide, $R^6$ is H, $R^7$ is OH, and X is O or S, proviso such molecule is not PIT-1, DM-PIT-1, PIT-1i-1, or PIT-1i-2, to reduce binding of PIP3 to pleckstrin homology domain, thereby selectively inhibiting the PIP3-dependent cellular signaling pathway in the cell.

In one embodiment, $R^1$ and $R^2$ are independently selected from H and —$CH_3$ (methyl), $R^3$ and $R^5$ are independently selected from H, —$CH_3$ (methyl), and —$CF_3$, $R^4$ is selected from H, —$CF_3$, phenyl, Cl, and Br, $R^6$ is H, $R^7$ is OH, and X is S.

In one embodiment, X is S.

In one embodiment, $R^4$ is substituted or unsubstituted phenyl. In one embodiment, $R^4$ is unsubstituted phenyl (i.e., $R^4$ is phenyl).

In one embodiment, $R^1$ and $R^2$ are independently selected from H and —$CH_3$ (methyl), $R^3$ and $R^5$ are independently selected from H, —$CH_3$ (methyl), and —$CF_3$, $R^4$ is selected from H, —$CF_3$, phenyl, Cl, and Br, $R^6$ is H, $R^7$ is OH, and X is S.

In one embodiment, $R^1$ and $R^2$ are independently selected from H and —$CH_3$ (methyl), $R^3$ and $R^5$ are independently selected from H, —$CH_3$ (methyl), and —$CF_3$, $R^4$ is selected from H, —$CF_3$, phenyl, Cl, and Br, $R^6$ is H, $R^7$ is OH, and X is S.

In one embodiment (PIT-3), each of $R^1$, $R^2$, $R^3$, and $R^5$ is —$CH_3$ (methyl), $R^4$ is Cl, $R^6$ is H, $R^7$ is OH, and X is S.

In one embodiment (PIT-4), each of $R^1$ and $R^2$ is —$CH_3$ (methyl), each of $R^3$ and $R^5$ is H, $R^4$ is —$CF_3$, $R^6$ is H, $R^7$ is OH, and X is S.

In one embodiment (PIT-5), each of $R^1$ and $R^2$ is —$CH_3$ (methyl), each of $R^3$ and $R^5$ is —$CF_3$, $R^4$ is H, $R^6$ is H, $R^7$ is OH, and X is S.

In one embodiment (PIT-6), each of $R^1$, $R^2$, $R^3$, and $R^5$ is —$CH_3$ (methyl), $R^4$ is Br, $R^6$ is H, $R^7$ is OH, and X is S.

In one embodiment (PIT-7), each of $R^1$ and $R^2$ is —$CH_3$ (methyl), each of $R^3$ and $R^5$ is H, $R^4$ is phenyl, $R^6$ is H, $R^7$ is OH, and X is S.

Formula II specifically embraces, without limitation, compounds designated herein as PIT-3, PIT-4, PIT-5, PIT-6, and PIT-7.

The method features selectively inhibiting a PIP3-dependent cellular signaling pathway in a cell. As used herein, "selectively inhibiting" in connection with a cell signaling pathway refers to inhibiting one particular cell signaling pathway largely to the exclusion of inhibiting any unrelated cell signaling pathway. In one embodiment, selectively inhibiting refers to inhibiting one particular cell signaling pathway essentially to the exclusion of inhibiting any unrelated cell signaling pathway. In one embodiment, selectively inhibiting refers to inhibiting one particular cell signaling pathway at least 10 times more effectively than inhibiting any unrelated cell signaling pathway. In one embodiment, selectively inhibiting refers to inhibiting one particular cell signaling pathway at least 20 times more effectively than inhibiting any unrelated cell signaling pathway. In one embodiment, selectively inhibiting refers to inhibiting one particular cell signaling pathway at least 50 times more effectively than inhibiting any unrelated cell signaling pathway. In one embodiment, selectively inhibiting refers to inhibiting one particular cell signaling pathway at least 100 times more effectively than inhibiting any unrelated cell signaling pathway.

As used herein, "inhibiting" refers to reducing by a measureable amount compared to a control amount measured under similar, e.g., physiological, conditions. In one embodiment the PIP3-dependent cellular signaling pathway is inhibited to less than or equal to 50% of control. In individual embodiments, the PIP3-dependent cellular signaling pathway is inhibited to less than or equal to 40%, 30%, 20%, 10%, 5%, and 1% of control.

In one embodiment the inhibiting includes inducing apoptosis of the cell. Apoptosis can be detected using any suitable method, including, without limitation, the well known methods of terminal deoxynucleotidyl transferase biotin-dUTP nick end labeling (TUNEL) assay, annexin V, morphology, immunohistochemistry, and electron microscopy, as well as any combination thereof.

In one embodiment the inhibiting includes inhibiting migration of the cell. Cell migration can be measured using any suitable method, including, without limitation, the well known methods of transwell migration, wound closure, and matrigel cell invasion assays such as are described in the examples below, as well as any combination thereof.

The cell is contacted with an effective amount of a compound of Formula I to reduce binding of pleckstrin homology domain to PIP3. As used herein, "reduce binding" refers to inhibiting a noncovalent binding interaction by at least a measureable amount as compared to a control amount of noncovalent binding interaction measured under similar conditions. The amount or extent of binding can be measured using any suitable method, including, for example, fluorescence polarization, fluorescent microscopy, or surface plasmon resonance (BIACore). In one embodiment the binding is reduced to less than or equal to 50% of a control amount of binding. In individual embodiments, the binding is reduced to less than or equal to 40%, 30%, 20%, 10%, 5%, and 1% of a control amount of binding.

The invention in one aspect is a method of treating cancer. The method includes the step of administering to a subject having a cancer an effective amount of a PIP3-specific non-phosphoinositide small molecule antagonist of binding of PIP3 to pleckstrin homology domain, thereby treating the cancer. As used herein, "cancer" refers to an uncontrolled growth of cells which interferes with normal functioning of at least one bodily organ or system. Cancers which migrate from their original location and seed vital organs can eventually lead to the death of the subject through the functional deterioration of the affected organs. In certain embodiments a cancer is a tumor. Hemopoietic cancers, such as leukemia, are able to outcompete the normal hemopoietic compartments in a subject, thereby leading to hemopoietic failure (in the form of anemia, thrombocytopenia, neutropenia, and any combination thereof) ultimately causing death.

A metastasis is a region of cancer cells, distinct in location from the primary tumor location, resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers include, but are not limited to, basal cell carcinoma; biliary tract cancer; bladder cancer; bone cancer; brain cancer and other central nervous system (CNS) cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's lymphoma and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In one embodiment a subject is a human.

A "subject having a cancer," as used herein, refers to a subject that exhibits at least one objective manifestation of cancer. In one embodiment a subject having a cancer is a subject that has been diagnosed as having a cancer and is in need of treatment thereof. Methods of diagnosing cancer are well known and need not be described here in any detail.

As used herein, "administering" has its usual meaning and encompasses administering by any suitable route of administration, including, without limitation, intravenous, intramuscular, intraperitoneal, subcutaneous, direct injection (for example, into a tumor), mucosal, inhalation, oral, and topical.

As used herein, the terms "treating" and "to treat" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "to treat" refer to performing an intervention that results in (a) inhibiting a condition or disease, e.g., slowing or arresting its development; or (b) relieving or ameliorating a condition or disease, e.g., causing regression of the condition or disease.

The invention in one aspect is a method of treating cancer. The method includes the step of administering to a subject having a cancer an effective amount of a compound of Formula II

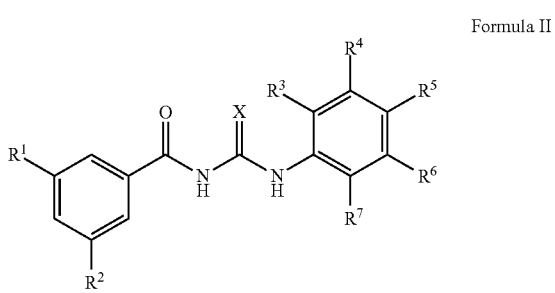

Formula II wherein
$R^1$ and $R^2$ are independently selected from H and C1-C5 alkyl, $R^3$ and $R^5$ are independently selected from H, C1-C5 alkyl, and —$CF_3$, $R^4$ is selected from H, —$CF_3$, C1-C12 alkyl, substituted or unsubstituted phenyl, $NO_2$, and halide, $R^6$ is H, $R^7$ is OH, and X is O or S, proviso such molecule is not PIT-1, DM-PIT-1, PIT-1i-1, or PIT-1i-2, to reduce binding of PIP3 to pleckstrin homology domain, thereby treating the cancer.

In one embodiment, $R^1$ and $R^2$ are independently selected from H and —$CH_3$ (methyl), $R^3$ and $R^5$ are independently selected from H, —$CH_3$ (methyl), and —$CF_3$, $R^4$ is selected from H, —$CF_3$, phenyl, Cl, and Br, $R^6$ is H, $R^7$ is OH, and X is S.

In one embodiment, X is S.

In one embodiment, $R^4$ is substituted or unsubstituted phenyl. In one embodiment, $R^4$ is unsubstituted phenyl (i.e., $R^4$ is phenyl).

In one embodiment, $R^1$ and $R^2$ are independently selected from H and —$CH_3$ (methyl), $R^3$ and $R^5$ are independently selected from H, —$CH_3$ (methyl), and —$CF_3$, $R^4$ is selected from H, —$CF_3$, phenyl, Cl, and Br, $R^6$ is H, $R^7$ is OH, and X is S.

In one embodiment, $R^1$ and $R^2$ are independently selected from H and —$CH_3$ (methyl), $R^3$ and $R^5$ are independently selected from H, —$CH_3$ (methyl), and —$CF_3$, $R^4$ is selected from H, —$CF_3$, phenyl, Cl, and Br, $R^6$ is H, $R^7$ is OH, and X is S.

In one embodiment (PIT-3), each of $R^1$, $R^2$, $R^3$, and $R^5$ is —$CH_3$ (methyl), $R^4$ is Cl, $R^6$ is H, $R^7$ is OH, and X is S.

In one embodiment (PIT-4), each of $R^1$ and $R^2$ is —$CH_3$ (methyl), each of $R^3$ and $R^5$ is H, $R^4$ is —$CF_3$, $R^6$ is H, $R^7$ is OH, and X is S.

In one embodiment (PIT-5), each of $R^1$ and $R^2$ is —$CH_3$ (methyl), each of $R^3$ and $R^5$ is —$CF_3$, $R^4$ is H, $R^6$ is H, $R^7$ is OH, and X is S.

In one embodiment (PIT-6), each of $R^1$, $R^2$, $R^3$, and $R^5$ is —$CH_3$ (methyl), $R^4$ is Br, $R^6$ is H, $R^7$ is OH, and X is S.

In one embodiment (PIT-7), each of $R^1$ and $R^2$ is —$CH_3$ (methyl), each of $R^3$ and $R^5$ is H, $R^4$ is phenyl, $R^6$ is H, $R^7$ is OH, and X is S.

In one embodiment the method results in or otherwise includes inhibiting growth of the cancer.

In one embodiment the method results in or otherwise includes inducing apoptosis of the cancer, i.e., induces apoptosis of cancer cells.

In one embodiment the method results in or otherwise includes inhibiting angiogenesis of the cancer, e.g., inhibits tumor angiogenesis.

In one embodiment the method results in or otherwise includes reducing metastasis of the cancer.

In one aspect the invention is a pharmaceutical composition which includes a therapeutically effective amount of a compound of Formula II

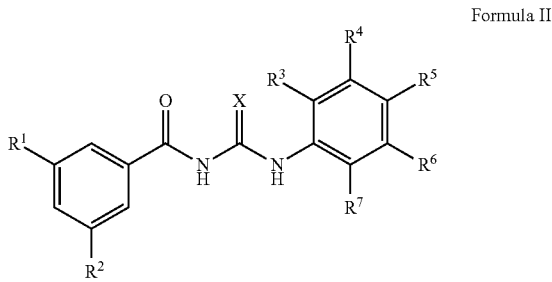

Formula II wherein
$R^1$ and $R^2$ are independently selected from H and C1-C5 alkyl,
$R^3$ and $R^5$ are independently selected from H, C1-C5 alkyl, and —$CF_3$,
$R^4$ is selected from H, —$CF_3$, C1-C12 alkyl, substituted or unsubstituted phenyl, $NO_2$, and halide,
$R^6$ is H,
$R^7$ is OH, and
X is O or S,
proviso such molecule is not PIT-1, DM-PIT-1, PIT-1i-1, or PIT-1i-2, and a water-soluble delivery vehicle.

In one embodiment,
$R^1$ and $R^2$ are independently selected from H and —$CH_3$ (methyl),
$R^3$ and $R^5$ are independently selected from H, —$CH_3$ (methyl), and —$CF_3$,
$R^4$ is selected from H, —$CF_3$, phenyl, Cl, and Br,
$R^6$ is H,
$R^7$ is OH, and
X is S.

In one embodiment, X is S.
In one embodiment, $R^4$ is substituted or unsubstituted phenyl. In one embodiment, $R^4$ is unsubstituted phenyl (i.e., $R^4$ is phenyl).
In one embodiment,
$R^1$ and $R^2$ are independently selected from H and —$CH_3$ (methyl),
$R^3$ and $R^5$ are independently selected from H, —$CH_3$ (methyl), and —$CF_3$,
$R^4$ is selected from H, —$CF_3$, phenyl, Cl, and Br,
$R^6$ is H,
$R^7$ is OH, and
X is S.

In one embodiment, $R^1$ and $R^2$ are independently selected from H and —$CH_3$ (methyl), $R^3$ and $R^5$ are independently selected from H, —$CH_3$ (methyl), and —$CF_3$, $R^4$ is selected from H, —$CF_3$, phenyl, Cl, and Br, $R^6$ is H, $R^7$ is OH, and X is S.

In one embodiment (PIT-3), each of $R^1$, $R^2$, $R^3$, and $R^5$ is —$CH_3$ (methyl), $R^4$ is Cl, $R^6$ is H, $R^7$ is OH, and X is S.

In one embodiment (PIT-4), each of $R^1$ and $R^2$ is —$CH_3$ (methyl), each of $R^3$ and $R^5$ is H, $R^4$ is —$CF_3$, $R^6$ is H, $R^7$ is OH, and X is S.

In one embodiment (PIT-5), each of $R^1$ and $R^2$ is —$CH_3$ (methyl), each of $R^3$ and $R^5$ is —$CF_3$, $R^4$ is H, $R^6$ is H, $R^7$ is OH, and X is S.

In one embodiment (PIT-6), each of $R^1$, $R^2$, $R^3$, and $R^5$ is —$CH_3$ (methyl), $R^4$ is Br, $R^6$ is H, $R^7$ is OH, and X is S.

In one embodiment (PIT-7), each of $R^1$ and $R^2$ is —$CH_3$ (methyl), each of $R^3$ and $R^5$ is H, $R^4$ is phenyl, $R^6$ is H, $R^7$ is OH, and X is S.

As used herein, a "delivery vehicle" refers to a pharmaceutically acceptable carrier to the surface of which can be attached, or within which can be enveloped, an active agent, suitable for delivery of the active agent to a desired site of action. Delivery vehicles specifically include, without limitation, nanoparticles, microparticles, liposomes, micelles, reverse micelles, cochleates, emulsomes, polymers, and virus-like particles. In one embodiment a delivery vehicle is prepared so as to envelop an active agent, for example, within a liposome or micelle.

A liposome is a tiny bubble or vesicle, made out of the same material as a cell membrane. Liposomes can be filled with drugs and used to deliver drugs for cancer and other diseases. Membranes are usually made of phospholipids, which are molecules that have a head group and a tail group. The head is attracted to water, and the tail, which is made of a long hydrocarbon chain, is repelled by water. In the presence of water, the heads are attracted to water and line up to form a surface facing the water. The tails are repelled by water and line up to form a surface away from the water.

When membrane phospholipids are disrupted, they can reassemble themselves into tiny spheres, smaller than a normal cell, either as bilayers or monolayers. The bilayer structures are liposomes.

Liposomes can be composed of naturally-derived phospholipids with mixed lipid chains (like egg phosphatidylethanolamine), or of pure surfactant components like dioleoylphosphatidylethanolamine (DOPE). Liposomes, usually but not by definition, contain a core of aqueous solution.

The monolayer structures are called micelles. Micelles are lipid spheres that typically contain no aqueous material. However, reverse micelles can be made to encompass an aqueous environment.

Cochleates are a lipid-based delivery system that enhances the potential for oral administration of hydrophobic drugs. They are stable phospholipid-cation crystalline structures consisting of a spiral lipid bilayer sheet with no internal aqueous space. See, for example, Santangelo R et al. (2000) *Antimicrob Agents Chemother* 44:2356-60.

An emulsome is a type of lipid particle considered as a hybrid between a liposome and an oil-in-water emulsion. Emulsome particles or solid-fat nanoemulsions consist of a type of lipid assembly comprising a hydrophobic core as in emulsion but surrounded by phospholipid bilayers that are characteristic of liposomes. The emulsome matrix increases the loading capacity of the active ingredients. Emulsomes are particularly well adapted for oral applications.

A virosome is a unilamellar phospholipid bilayer vesicle with a mean diameter of about 150 nm. Essentially, virosomes represent reconstituted empty influenza virus envelopes, devoid of the nucleocapsid including the genetic material of the source virus. Virosomes are not able to replicate but are pure fusion-active vesicles. In contrast to liposomes, virosomes contain functional viral envelope glycoproteins: influenza virus hemagglutinin (HA) and neuraminidase (NA) intercalated in the phospholipid bilayer membrane.

In one embodiment the composition is formulated as nanoparticles. As used herein, the term "nanoparticle" refers to a particle, which can be solid or hollow, which is characterized by a maximum dimension along any axis between 1 nm and less than about 1 μm, e.g., 950 nm. In one embodiment a nanoparticle is characterized by a maximum dimension along any axis between 1 nm and 10 nm. In one embodiment a nanoparticle is characterized by a maximum dimension along any axis between 10 nm and 100 nm. In one embodiment a nanoparticle is characterized by a maximum dimension along any axis between 100 nm and less than about 1 μm, e.g., 950 nm. In one embodiment a nanoparticle is characterized by a maximum dimension along any axis of less than about 1 μm, e.g., 950 nm. Nanoparticles can be solid phase or liquid phase, and they can be biodegradable or nonbiodegradable. In one embodiment a nanoparticle for use in accordance with the instant invention is a biodegradable nanoparticle. In one embodiment a nanoparticle is a liposome. In one embodiment a nanoparticle is a micelle.

In one embodiment the nanoparticles include polyethylene glycol-phosphoethanolamine (PEG-PE) micelles, loaded with active agent, such as are described in Example 9 below.

In one embodiment the composition is formulated as microparticles. As used herein, the term "microparticle" refers to a particle, which can be solid or hollow, which is characterized by a maximum dimension along any axis between 1 μm and 100 μm. In one embodiment a microparticle is characterized by a maximum dimension along any axis between 1 μm and 10 μm. In one embodiment a microparticle is characterized by a maximum dimension along any axis between 10 μm and 100 μm. In one embodiment a microparticle is characterized by a maximum dimension along any axis of less than or equal to 100 μm. Microparticles can be solid phase or liquid phase, and they can be biodegradable or non-biodegradable. In one embodiment a microparticle for use in accordance with the instant invention is a biodegradable microparticle. In one embodiment a microparticle is a liposome. In one embodiment a microparticle is a micelle.

Solid phase nanoparticles and microparticles may be particles formed from biocompatible naturally occurring polymers, synthetic polymers or synthetic copolymers, which may include or exclude nanoparticles and microparticles formed from agarose or cross-linked agarose, as well as other biodegradable materials known in the art. Biodegradable solid phase nanoparticles and microparticles may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5]undecane (DETOSU) or poly(anhydrides), such as poly(anhydrides) of sebacic acid) under mammalian physiological conditions.

Nanoparticles and microparticles may also be liquid phase (e.g., oil- or lipid-based), such liposomes, iscoms (immune-stimulating complexes, which are stable complexes of cholesterol, and phospholipid, adjuvant-active saponin) without antigen, or droplets or micelles found in oil-in-water or oil-in-water-in-oil emulsions, provided the liquid phase nanoparticles and microparticles are biodegradable. Biodegradable liquid phase nanoparticles and microparticles typically incorporate a biodegradable oil, a number of which are known in the art, including squalene and vegetable oils.

Nanoparticles and microparticles are typically spherical in shape, but nanoparticles and microparticles which deviate from spherical shape are also acceptable (e.g., ellipsoid, rod-shaped, etc.).

Solid phase nanoparticles and microparticles are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly (glycolic acid), poly(D,L-lactic-co-glycolic acid) and poly (caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid nanoparticles or microparticles are then separated by centrifugation or filtration, and dried, for example, by lyophilization or application of vacuum, before storing at 4° C.

Physico-chemical characteristics such as mean size, size distribution and surface charge of dried nanoparticles and microparticles may be determined. Size characteristics are determined, for example, by dynamic light scattering technique and the surface charge was determined by measuring the zeta potential.

In one embodiment the water-soluble delivery vehicle comprises a targeting agent. As used herein, a "targeting agent" refers to a molecule or other chemical moiety which is capable of selectively binding to a molecule or molecular complex expressed on the surface of a cell to which it is desired to deliver an active agent. Targeting agents can include, without limitation, antibodies or antigen-binding fragments of antibodies, receptors (for co-receptors expressed on target cells), and co-receptors (for receptors expressed on target cells). In one embodiment the targeting agent is covalently linked to the delivery vehicle. In one embodiment the targeting agent is non-covalently linked to the delivery vehicle. Non-covalent linkages can be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the targeting agent.

Linkage between the targeting agent and delivery vehicle can be direct (e.g., via disulfide bond between sulfhydryls on the targeting agent and delivery vehicle) or the constituents can be linked by a crosslinking moiety of one or more atoms separating the bonds to the targeting agent and delivery vehicle. Non-covalent complexes generally include a targeting agent that has been modified to allow binding to the delivery vehicle (e.g., by addition of a cholesterol moiety to the targeting agent to allow hydrophobic binding to oil- or lipid-based delivery vehicle).

In one embodiment the composition is formulated as nanoparticles.

In one embodiment the nanoparticles include polyethylene glycol-phosphoethanolamine (PEG-PE) micelles, loaded with active agent, such as are described in Example 9 below.

In one embodiment the water-soluble delivery vehicle includes a targeting agent.

PITs can be combined with other therapeutic agents. The PIT and other therapeutic agent may be administered simultaneously or sequentially. When the other therapeutic agents are administered simultaneously, they can be administered in the same or separate formulations, but they are administered at the same time. The other therapeutic agents are administered sequentially with one another and with PIT, when the administration of the other therapeutic agents and the PIT is temporally separated. The separation in time between the administration of these compounds may be a matter of minutes or it may be longer.

Other therapeutic agents which may be combined with PIT include but are not limited to TRAIL and anti-cancer therapies.

Tumor necrosis factor (TNF)-related apoptosis-inducing ligand (TRAIL), also known as Apo2L, is a 281 amino acid-long member of the TNF family of cytokines that promotes apoptosis. Sheridan J P et al. (1997) *Science* 277:818-21. TRAIL induces apoptosis via death receptors in a wide variety of tumor cells but not in normal cells. Normal cells, but apparently not cancer cells, produce a "decoy receptor" that binds TRAIL, but is incapable of transmitting its death message to the cell interior. It has been reported that TRAIL treatment results in significant growth suppression of TRAIL-sensitive human cancer xenografts in mice. Nagane M et al. (2001) *Apoptosis* 6:191-7. It has also been reported that TRAIL receptor (TRAIL-R) deficiency in mice promotes susceptibility to chronic inflammation and tumorigenesis. Finnberg N et al. (2008) *J Clin Invest* 118:11-23.

The PITs may also be administered in conjunction with an anti-cancer therapy. Anti-cancer therapies include cancer medicaments, radiation, and surgical procedures. As used herein, a "cancer medicament" refers to an agent which is administered to a subject for the purpose of treating a cancer. As used herein, "treating a cancer" includes preventing the development of a cancer, reducing the symptoms of cancer, and/or inhibiting the growth of an established cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

A chemotherapeutic agent can be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MM1270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32Nalrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCI, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2' deoxycoformycin), Semustine (methyl-CCNU), Teniposide (VM-26) and Vindesine sulfate, but it is not so limited.

An immunotherapeutic agent may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA, but it is not so limited.

A cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vacine, TA-HPV, TA-CIN, DISC-virus and ImmuCyst/TheraCys, but it is not so limited.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular PIT being administered, the size of the subject, or the severity of the disease or condition. One of ordinary skill in the art can empirically determine the effective amount of a particular PIT and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the drug. "Dose" and "dosage" are used interchangeably herein.

Generally, daily oral doses of active compounds will be from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

For any compound described herein the therapeutically effective amount can be initially determined from animal models. A therapeutically effective dose can also be determined from human data for PITs which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the PIT can be administered to a subject by any mode that delivers the PIT to the desired surface. Administering the pharmaceutical composition of the present invention may be accomplished by any means known to the skilled artisan. Routes of administration include but are not limited to intravenous, intramuscular, intraperitoneal, subcutaneous, direct injection (for example, into a tumor), mucosal, inhalation, oral, and topical.

For oral administration, the compounds (i.e., PITs, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis (1981) "Soluble Polymer-Enzyme Adducts" In: *Enzymes as Drugs*, Hocenberg and Roberts, eds., Wiley-Interscience, New York, N.Y., pp. 367-383; Newmark et al. (1982) *J Appl Biochem* 4:185-9. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the PIT (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the PIT (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents can be used and can include benzalkonium chloride and benzethonium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the PIT or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the PITs (or derivatives thereof). The PIT (or derivative) is delivered to the lungs of a mammal while inhaling and traverses across the lung epithelial lining to the blood stream. Other reports of inhaled molecules include Adjei et al. (1990) *Pharmaceutical Research* 7:565-569; Adjei et al. (1990) *International Journal of Pharmaceutics*, 63:135-144 (leuprolide acetate); Braquet et al. (1989), *Journal of Cardiovascular Pharmacology*, 13(suppl. 5):143-146 (endothelin-1); Hubbard et al. (1989) *Annals of Internal Medicine*, 3:206-212 (α1-antitrypsin); Smith et al. (1989) *J. Clin. Invest.* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al. (1988) *J. Immunol.* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of PIT (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified PIT may also be prepared in different formulations depending on the type of chemical modification or the type of device employed.

Formulations suitable for use with a nebulizer, either jet or ultrasonic, will typically comprise PIT (or derivative) dissolved in water at a concentration of about 0.1 to 25 mg of biologically active PIT per mL of solution. The formulation may also include a buffer and a simple sugar (e.g., for PIT stabilization and regulation of osmotic pressure). The nebulizer formulation may also contain a surfactant, to reduce or prevent surface induced aggregation of the PIT caused by atomization of the solution in forming the aerosol.

Formulations for use with a metered-dose inhaler device will generally comprise a finely divided powder containing the PIT (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing PIT (or derivative) and may also include a bulking agent, such as lactose, sorbitol, sucrose, or mannitol in amounts which facilitate dispersal of the powder from the device, e.g., 50 to 90% by weight of the formulation. The PIT (or derivative) should most advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) *Science* 249:1527-33, which is incorporated herein by reference.

The PITs and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a PIT and optionally therapeutic agents included in a pharmaceutically-acceptable carrier. The term "pharmaceutically-acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the PIT, may be provided in particles. Particles as used herein means nanoparticles or microparticles (or in some instances larger particles) which can consist in whole or in part of the PIT or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the PIT in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The present invention is further illustrated by the following examples, which in no way should be construed as further limiting. The entire contents of all the references (including literature references, issued patents, published patent applications, and co-pending patent applications) cited throughout this application are hereby expressly incorporated by reference.

EXAMPLES

Materials

PIT-1 analogs DM-PIT-1, PIT-1i-1, and PIT-1i-2 were obtained from Chembridge (San Diego, Calif.). PIT-2 was obtained from Ryan Scientific (Mt. Pleasant, Calif.). PIT-1 analogs PIT-3, PIT-4, PIT-5, PIT-6, and PIT-7 were synthesized using conventional organic chemistry techniques, in accordance with Example 15. Tetramethylrhodamine (TMR)-labeled phosphoinositides were purchased from Echelon Biosciences. Akt inhibitor VIII and LY294002 were purchased from Calbiochem. zVAD.fmk and TRAIL (Killer-TRAIL™) were obtained from Axxora. Matrigel was obtained from BD Biosciences. Propidium iodide (PI) was obtained from Roche. bFGF was obtained from R&D Systems. EZ-detect™ Racl activation kit was obtained from Pierce Biotechnology. Sytox Green and secondary Alexa 488—conjugated antibodies were purchased from Molecular Probes. Secondary horseradish peroxidase (HRP)-conjugated antibodies for Western blot assays were obtained from Southern Biotech. Mouse anti-β-tubulin antibody was purchased from Stressgene. Rabbit anti-LC3 antibody was obtained from MBL. Goat anti-CD31 antibody was obtained from Santa Cruz. All the other phosphoric antibodies including rabbit anti-Akt (Thr308 or Ser473), anti-p70S6K (Thr389 or Ser371), anti-p90S6K (Ser380), anti-S6 (Ser235/236), anti-Gsk-3-β (Ser9), anti-4E-BP1 (Ser65 or Thr70), anti-FKHR (Ser256), anti-MDM2 (Ser166), anti-mTOR (Ser2448), anti-TSC2 (Thr1462), anti-Akt substrate (Ser/Thr), anti-AMPK (Thr172), anti-ACC (Ser79), and non-phosphoric antibodies including anti-caspase-3, anti-PARP antibodies, were purchased from Cell Signaling Technology. IGF-1 and PDGF, tetramethyl rhodamine isothiocyanate (TRITC)-labeled phalloidin, mouse anti-acetylated tubulin antibody, and all other reagents and chemicals were obtained from Sigma. Btk PH domain-GFP vector was purchased from Signagen Laboratories.

PLC-delta PH domain-GFP vector was a generous gift of Dr. Or Gozani, Stanford University. Akt PH domain-GFP, VAV2-GFP and VAV3-GFP vectors were generous gifts of Dr. Joanne Brugge, Harvard Medical School. WAVE2-GFP was a generous gift of Dr. Rachel Joy Buchsbaum, Tufts University. WAVE3-GFP was a generous gift of Dr. Khalid Sossey-Alaoui, Roswell Park Cancer Institute. Human Akt PH domain a.a. 1-123 and human PDK1 PH domain a.a. 411-557 were cloned by PCR amplification into BamH1/Eco RI sites of pGEX-6P-1 vector (GE Healthcare). For NMR experiments, His6-Akt PH123 was prepared by cloning corresponding PCR fragment between Nde I and Eco RI sites of pET-28 vector (Novagen). Recombinant proteins were expressed in BL21(DE3) *E. coli*. Expression was induced by addition of 100 µM IPTG for 16 hr at 25° C. Proteins were purified using glutathione-sepharose (GE Healthcare) or Ni-NTA beads (Qiagen) according to manufacturer's recommendations and dialyzed overnight against 50 mM Tris-HCl (pH 7.5), 150 mM NaCl, and 5 mM β-mercaptoethanol (b-ME) buffer.

Cells and Cell Culture

Human and mouse cancer cell lines (U87MG, SUM159, A549, MDA-MB-231, 4T1, B16-F10) and human umbilical vein endothelial cells (HUVEC) were purchased from the American Type Culture Collection (Rockville, Md., USA). Mouse adult lung fibroblasts (Akt-deficient and Akt1-expressing) were a generous gift of Dr. Philip Tsichlis (Tufts University). Maroulakou I et al. (2007) *Cancer Res* 67:167-77. Bax/Bak double knockout mouse embryonic fibroblasts (Wei M C et al. (2001) *Science* 292:727-30) and matched wild-type cells were a generous gift of Dr. Stanley Korsmeyer (Dana-Farber Cancer Center). B16-F10, U87MG, 4T1, A549, MDA-MB-231 and fibroblast cells were cultured in DMEM medium with 10% fetal bovine serum (FBS). SUM159 was maintained in Ham's F-12 medium with 5% FBS, 5 µg/ml insulin, and 1 µg/ml hydrocortisone. HUVEC cells were cultured in M199 medium with 20% FBS, 20 µg/ml ECGS, and 50 µg/ml heparin. All media were supplemented with 100 units/ml penicillin, 100 µg/ml streptomycin, and 2 mM glutamine. All cells were cultured in a humidified atmosphere of 95% air and 5% $CO_2$ at 37° C.

Example 1

Identification of PIT-1 and PIT-2 as Specific PIP3 Inhibitors

In order to identify compounds that disrupt the interaction between PIP3 and PH domains, a high-throughput fluorescence polarization (FP)-binding assay was developed using recombinant 1-123 amino acid N-terminal fragment of human Akt1 (also referred to herein simply as Akt), encompassing the PH domain (PH123 protein), and fluorescent NBD-labeled PIP3 molecule. The amino acid sequence of human Akt1 is publicly available as, for example, GenBank Accession No. NP_001014432.1 (SEQ ID NO:1), and the corresponding DNA sequence is publicly available as, for example, GenBank Accession No. NM_001014432. Briefly, 5 µM recombinant GST fusion proteins containing 1-123 a.a. N-terminal fragment of human Akt1 (PH 123) or 100 nM 441-551 a.a. region of human PDK1 were incubated with 15 nM TMR-labeled PIP3, PIP2, or PIP5 in buffer containing 50 mM Tris-HCl (pH 7.5), 150 mM NaCl, and 5 mM b-ME for 15 min at room temperature in the dark. FP values were determined using Wallac Victor 3 plate reader. For the primary screen, 50,000 diverse small molecules from Harvard Institute of Chemistry and Cell Biology were screened (iccb.med.harvard.edu). Incubations were carried out for 1 hr. For secondary assays, PIT compounds were added at various concentrations (6.25, 12.5, 25, 50, 100, 150 and 200 µM), followed by a 30 min incubation. The inhibition rates were calculated as inhibition rate=[1−(compound-treated group/control group)]×100%, and $IC_{50}$ value was determined using Origin6 software (MicroCal, LLC, Northampton, Mass.).

To validate this assay it was determined that introducing the mutation R86A, which was previously shown to disrupt PIP3-PH interaction (Thomas C C et al. (2002) *Curr Biol* 12:1256-62), into PH123 completely abrogated fluorescent PIP3 binding (FIG. 1).

Figure 3:
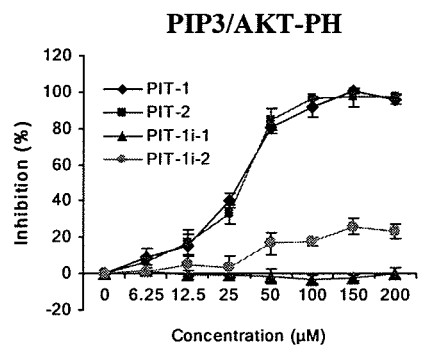
FIG. 3 is a graph depicting concentration-dependent competitive inhibition of PIP3-PH domain interaction by PIT-1 and PIT-2. 15 nM TMR-conjugated PIP3 were incubated with 5 μM GST-PH domain of Akt in the presence or absence of the indicated concentrations of PITs (0-200 μM) for 30 min, followed by FP measurement.

Screen of ~50,000 diverse small molecules resulted in the selection of two distinct inhibitors of PIP3/PH domain binding, which were termed PIT-1 and PIT-2 (FIG. 2). These molecules disrupted PIP3/Akt PH domain binding with $IC_{50}$=28.14 µM for PIT-1 and 31.52 µM for PIT-2 (FIG. 3). Although PIT-2 showed similar activity compared to PIT-1, PIT-2, in contrast to PIT-1, displayed limited stability even in dimethylsulfoxide (DMSO). Accordingly, many of the experiments described herein used PIT-1 and used freshly prepared PIT-2 solution to confirm major conclusions.

Analysis of several analogs of PIT-1 suggested that thiourea and hydroxyl groups are important for activity in vitro. The same analysis also provided closely related inactive analogs of PIT-1, termed PIT-1i-1 and PIT-1i-2 (FIG. 2), which were used as negative controls throughout the studies described herein.

Figure 5:
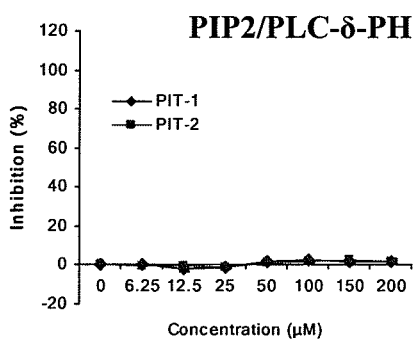
FIG. 5 is a graph depicting specificity and concentration-dependent competitive inhibition of PIP3-PH domain interaction by PIT-1 and PIT-2. 15 nM TMR-conjugated PIP2 were incubated with 100 nM PLC-δ PH domain in the presence or absence of the indicated concentrations of PITs (0-200 μM) for 30 min, followed by FP measurement.

Results of these studies indicate that PIT-1 and PIT-2 are selective non-phosphoinositide-related antagonists of PIP3/PH domain binding. Similar to the Akt PH domain, PIT-1 and PIT-2 inhibited binding of PIP3 to the PH domain of PDK1 (FIG. 4). In contrast to the PIP3-specific Akt and PDK1 PH domains, however, PITs failed to inhibit the interaction between PIP2 and PH domain of PLC-δ, which is known to have a preference for this lipid. Czech M P et al. (2000) *Cell* 100:603-6; Rameh L E et al. (1999) *J Biol Chem* 274:8347-50. (FIG. 5).

The concentration-dependent inhibitory effect of PIT-1 on PIP3/PH123 binding was further confirmed using a different method, a lipid overlay assay (Rameh L E et al. (1999) *J Biol Chem* 274:8347-50), which detects the binding of recombinant proteins to the membrane-spotted lipids.

To further characterize the mode of action of PIT-1, NMR-based analyses of PIT-1 binding to the PH domain of Akt were performed. It was determined that PIT-1 induces significant changes in the 2D HSQC $^1H$-$^{15}N$ correlation spectrum of His6-Akt123, indicative of the direct PIP3/PH domain binding. Similar results were also obtained with PIT-2. PIT-1 was further titrated to identify residues primarily affected by the small molecule binding. Using published Akt2 HSQC peak assignments (Auguin D et al. (2004) *J Biomol NMR* 28:137-55), it was observed that the residues Trp22 (W22), Tyr26 (Y26), and Asn54 (N54), located in the PIP3 binding pocket of the Akt PH domain, are primarily affected by PIT-1. Changes in other crosspeak signals were observed only at the 2× access of PIT-1.

To validate the conclusion that PIT-1 interacts with the PIP3-binding site of Akt PH domain, similar experiments were also performed using R86A mutant of the PH domain, which lacks PIP3 binding activity. It was found that PIT-1 had no effect on this protein, confirming PIP3-mimetic nature of PIT-1. Furthermore, PIT-1 did not elicit any changes in HSQC spectra of the unrelated proteins Bcl-xL and eIF-1, confirming specificity of the PIT-1 binding.

Using this information, the binding pose of PIT-1 on the surface of the Akt PH domain was proposed. In a three-dimensional model, PIT-1 binding site overlaps with the PIP3 binding site on Akt PH domain. Consistent with NMR data, Trp22 (W22) and Tyr26 (Y26) flank RPR motif that interacts with 3-phosphate of PIP3 and nitro group of PIT-1, while Asn54 (N54) packs against terminal phenyl group of PIT-1 and does not interact with PIP3.

Example 2

PIT-1 and PIT-2 Inhibit PIP3-Mediated Signaling

Figure 6:
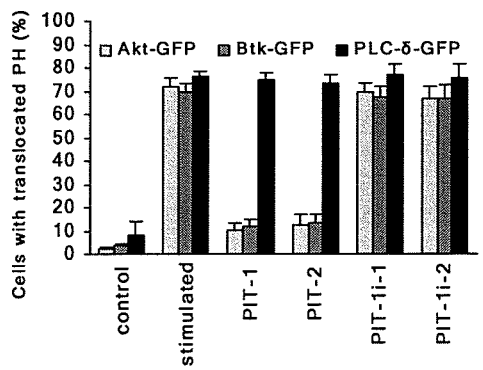
FIG. 6 is a bar graph depicting that PITs inhibit growth factor-induced plasma membrane translocation of the PIP3 specific Akt and Btk PH domains, but do not affect translocation of the PIP2-specific PLC-δ PH domain. Cells were transfected with the corresponding GFP-fusion vectors, serum starved overnight, and incubated with 100 μM PITs or PIT-1 is for 2 hr, followed by stimulation with 100 ng/ml PDGF or 250 ng/ml PMA for 5 min. The translocation was analyzed using fluorescent microscope and was quantitated by counting the number of cells with translocated PH domains in five random fields.

To begin characterizing cellular activity of PITs, a PH domain translocation assay was performed, measuring PIP3-induced association of GFP-fused PH domains with the plasma membrane. This method provides useful means for monitoring status of the PH domain/PIP3 binding in the intact cells. Varnai P et al. (1999) *J Biol Chem* 274:10983-9. Several PH-domain-containing proteins, which are known to bind PIP3 specifically and efficiently, were examined. As shown in FIG. 6, both PIT-1 and PIT-2 significantly inhibited the translocation of Akt and Btk (and similarly VAV2) to the plasma membrane in response to PDGF stimulation. Interestingly, these same compounds also suppressed the plasma membrane translocation of WAVE2, which lacks PH domain but binds PIP3 through the basic region. Oikawa T et al. (2004) *Nat Cell Biol* 6:420-6. This result illustrates PIP3-mimetic activity of PITs.

In contrast, no inhibitory effect was observed on the cellular localization of PLC-δ PH domain, which is specific for PIP2. This result indicates that PIT-1 does not disrupt PIP2/PH domain binding and is consistent with the results of separate FP analysis. Neither PIT-1i-1 nor PIT-1i-2, two closely related inactive analogs of PIT-1 (FIG. 2), inhibited translocation of Akt and Btk PH domains.

The effect of PIT-1 on PIP3-mediated signaling was examined in U87MG glioblastoma cells, which show elevated basal levels of PIP3 due to the loss of PTEN. Pore N et al. (2003) *Cancer Res* 63:236-41. It was determined that both PIT-1 and PIT-2 suppressed activity of the PI3K-PDK1-Akt pathway in these cells by looking at well established PI3-kinase/PIP3-regulated phosphorylation events. In contrast, inactive PIT analogs PIT-1i-1 and PIT-1i-2 failed to inhibit PDK1/Akt signaling. Similarly, PIT-1 significantly suppressed PI3K-PDK1-Akt signaling in growth factor-stimulated aggressive breast carcinoma SUM159 cells. These data confirm that PIT-1 and PIT-2 inhibit PIP3-dependent signaling in cells.

Example 3

PIT-1 and PIT-2 Preferentially Reduce Viability of PTEN-Deficient Glioblastoma Cells Based on the critical role of PIP3-dependent Aid signaling in the regulation of cell survival, the effect of PIT-1 on the cancer cell viability was tested. Cancer cells were seeded into 96-well plates (white plates for ATP assay; black plates for fluorescent assay; clear plates for MTS assay) at the density of $5-10 \times 10^3$ cells per well in 100 µl of the appropriate media. Compounds were added at a series of concentrations and incubated for different times. For the ATP assay, a luminescence-based commercial kit (CellTiter-Glo, Promega, Madison, Wis.) was used. Thirty microliters of cell lysis/ATP detection reagent was added to each well, mixed for 10 min at room temperature, and the luminescence was measured using a Wallac Victor 3 plate reader (Perkin-Elmer, Wellesley, Mass.). For the MTS assay, a CellTiter 96 AQueous Non-Radioactive Cell Proliferation Assay Kit (Promega, Madison, Wis., USA) was used. Twenty microliters of the combined MTS/PMS solution was added into each well, incubated for 4 hr at 37° C., and the absorbance at 490 nm was measured using a Wallac Victor 3 plate reader. For the Sytox cell death assay, measuring loss of plasma membrane integrity, cells were incubated with 1 µM Sytox Green reagent (Molecular Probes, Eugene, Oreg.) for 30 min at 37° C. and the fluorescence intensity was measured using Wallac Victor 3 plate reader with excitation at 485 nm and emission at 545 nm. Next, 5 µl of 20% (v/v) Triton X-100 solution was added to each well and incubated for 1 hr at 37° C., and the signal was measured again. The ratio of values (percentage of dead cells in each well) before and after Triton X-100 treatment was calculated and normalized to the relevant controls not subjected to the cytotoxic stimuli. $IC_{50}$ values were determined using Origin6 software (MicroCal, LLC, Northampton, Mass.).

Figure 7:
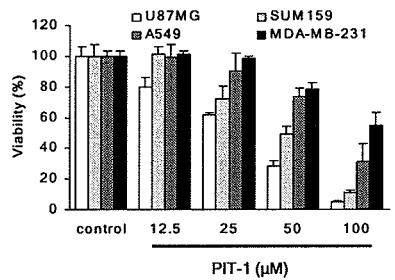
FIG. 7 is a bar graph depicting that PIT-1 reduces viability of multiple types of cancer cells. Different cancer cell lines U87MG, SUM 159, A549, and MDA-MB-231 were incubated with the indicated concentrations of PIT-1 (12.5-100 μM) for 48 hr. Cell viability was determined using ATP assay.
Figure 8:
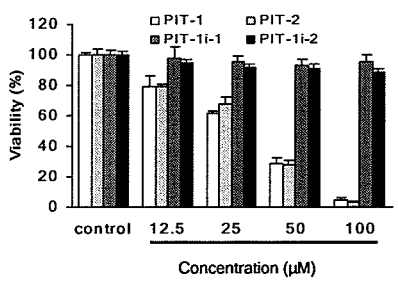
FIG. 8 is a bar graph depicting that both PIT-1 and PIT-2, but not inactive derivatives PIT-1i-1 and PIT-1i-2, reduce viability of U87MG cells. U87MG cells were incubated with PITs (12.5-100 μM) for 48 hr. Cell viability was determined using ATP assay.

Both PIT-1 and PIT-2 reduced viability of multiple cancer cell lines (e.g., mouse melanoma B16 cells, human Jurkat T cells, rat Lewis lung carcinoma cells, human lung carcinoma A549 cells, mouse and human breast carcinoma 4T1, SUM-159, and MDA-MB-231 cells, etc.) in a dose- and time-dependent manner using either MTS or ATP cell viability assays (FIGS. 7,8). In addition, PIT-1 also suppressed long-term colony formation by U87MG cells. Exposure of the cells to PITs resulted in eventual cell rounding, loss of adhesion, and cell death. In contrast, the inactive analogs PIT-1i-1 and PIT-1i-2 did not induce loss of viability (FIG. 3).

Figure 9:
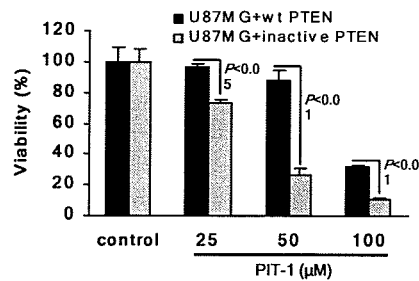
FIG. 9 is a bar graph depicting that the toxicity of PIT-1 is more pronounced in PTEN-deficient U87MG cells expressing R130M inactive mutant of PTEN, compared to control cells expressing wild-type (wt) PTEN. After treatment with 25, 50, or 100 μM PIT-1 for 48 hr, cell death was analyzed using Sytox cell death assay.

Previous reports suggested that constitutive exposure of transformed cells to oncogenic signaling results in profound changes in cellular regulation, rendering cancer cells hypersensitive to the disruption of oncogenic signals ("oncogene addiction"). Shaughnessy J D (2008) Nature 454:172-3; Weinstein I G (2002) Science 297:63-4. Therefore, the possibility that PIT-1 may cause preferential cell death in the cells containing elevated PIP3 levels was examined. Comparison was made between PIT-1 effect on the viability of PTEN-deficient glioblastoma U87MG cells stably re-expressing wild-type and R130M inactive mutant of PTEN. Li D M et al. (1998) Proc Natl Acad Sci USA 95:15406-11. It was observed that the toxicity of PIT-1 was more pronounced in PTEN-deficient U87MG cells lacking PTEN activity (FIG. 9). This observation is consistent with the notion that PTEN-deficient cancer cells become overly dependent on PIP3 signaling and, therefore, are hypersensitive to disruption of this pathway compared to wild-type PTEN-expressing cells. Neshat M S et al. (2001) Proc Natl Acad Sci USA 98:10314-9. Furthermore, the loss of viability caused by both PIT-1 and PIT-2 was more pronounced ($P<0.01$) in SV40-transformed mouse adult lung fibroblasts expressing Akt1 compared to the triple knockout cells deficient in all Akt isoforms (Akt1-3), confirming the contribution of Akt to the PIT-1-induced cell death. This effect was comparable to that of Akt kinase inhibitor VIII.

Figure 10:
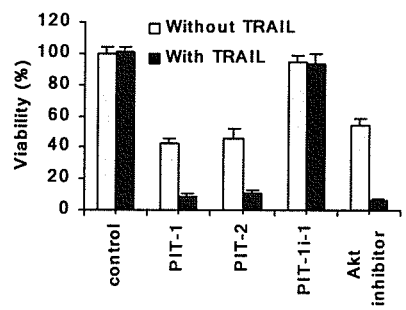
FIG. 10 is a bar graph depicting that PITs, as well as Akt inhibitor VIII, sensitize U87MG cells to killing by TRAIL. U87MG cells were incubated with 50 μM PIT-1, PIT-2, PIT-1i-1 or 10 μM Akt inhibitor VIII in the presence or absence of 10 ng/ml TRAIL for 48 hr, followed by cell viability analysis using ATP assay.

Upregulation of PI3K/Akt signaling is an important mechanism of chemoresistance of cancer cells. Blume-Jensen P et al. (2001) Nature 411:355-65; Osaki M et al. (2004) Apoptosis 9:667-76. In particular, inhibition of PI3K and Akt was shown to sensitize cancer cells to killing by the TNFα family member, TRAIL. Puduvalli V K et al. (2005) Apoptosis 10:233-43 TRAIL represents a particularly promising anti-cancer agent due to its intrinsic selectivity towards cancer cells which is associated with the expression of the decoy receptors by many (but not all) normal cells. Abe K et al. (2000) Ann NY Acad Sci 926:52-63. At the same time, overactivation of intracellular anti-apoptotic mechanisms has been shown to attenuate cancer cell sensitivity to TRAIL. Oka N et al. (2005) Cancer Res 65:7546-53. While U87MG cells are indeed entirely resistant to TRAIL, it was found that PIT-1 substantially sensitized U87MG cells to killing by TRAIL (FIG. 10). Similar results were obtained using PIT-2 as well as Akt kinase inhibitor VIII, but not PIT-1i-1 (FIG. 10). Furthermore, this effect was again significantly more pronounced in U87MG cells expressing inactive PTEN compared to that in cells expressing wild-type PTEN. The killing of U87MG cells by PIT-1 was more pronounced than that by the PI3K inhibitor LY294002, which may be explained by the direct inhibition of PIP3 activity at its sites of action by PIT-1.

To further confirm the mode of action of PIT-1 in the cells is directly related to the inhibition of PIP3/Akt PH domain interaction, induction of cell death in cells overexpressing constitutively active Akt lacking PH domain, but containing a membrane-targeting myristoylation signal, was tested. It was found that overexpression of PH domain-deficient Akt indeed significantly protected U87MG cells from PIT-1 killing ($P<0.05$). Similar results were also obtained with PIT-2. These results confirm that inhibition of Akt contributes to the killing of U87MG cells by PITs, although partial inhibition of cell death by Myr-Akt expression suggests that other targets may also be involved. This is not unexpected, considering that another PIT-1 target, PDK1, regulates cell survival through both Akt-dependent and Akt-independent pathways.

Taken together, these data indicate that PITs represent a novel class of PIP3 signaling antagonists which are capable of reducing viability of cancer cells directly and synergizing with activity of other anti-cancer agents.

Example 4

PIT-1 and PIT-2 Induce Apoptosis and Metabolic Stress

Figure 11:
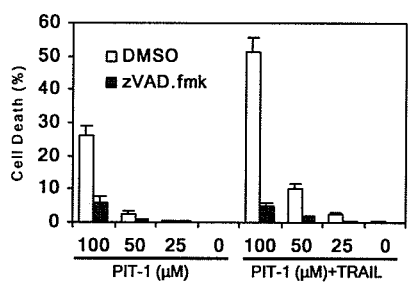
FIG. 11 is a bar graph depicting that cell death triggered by PIT-1 alone or in combination with TRAIL is inhibited by pan-caspase inhibitor zVAD.fmk. U87MG cells were incubated with or without 100 μM zVAD.fmk together with PIT-1 (25, 50, 100 μM) in the presence or absence of 10 ng/ml TRAIL for 24 hr, and analyzed by Sytox cell death assay.

Since PI3K/PIP3/Akt signaling plays a critical role in the inhibition of apoptosis (Datta S R et al. (1999) Genes Dev 13:2905-27), the possibility that PITs induce apoptosis was examined. Cell death triggered by PIT-1 and PIT-2 alone or in combination with TRAIL was inhibited by a pan-caspase inhibitor zVAD.fmk (FIG. 11). Proapoptotic Bcl-2 family members Bax and Bak are important mediators of apoptosis. Wei M C et al. (2001) *Science* 292:727-30. It was found that killing of cells by PIT-1 and PIT-2 was reduced in Bax/Bak double knockout cells compared with wild-type cells. Cell death induced by PIT-1 showed multiple features characteristic for apoptosis. Namely, PIT-1 and PIT-2 treatment caused a significant increase in subG1 DNA content in cells (P<0.01). In addition, the nuclei of treated cells had a condensed and fragmented morphology that is characteristic of apoptosis. Finally, Western blot analysis showed that PIT-1 induced the cleavage/activation of the critical apoptosis executioner molecule, caspase-3, leading to the processing of its substrate, poly (ADP-ribose) polymerase (PARP). These data indicate activation of apoptosis by PIT molecules, consistent with inhibition of the anti-apoptotic activity of the Akt signaling pathway. Non-apoptotic mechanisms of cell death may also play some additional, albeit less important, role in PIT-induced killing, as some cell death was still observed in Bax/Bak-deficient cells and in the presence of zVAD.fmk.

Changes in cell metabolism have emerged in recent years as an important component of PI3K/PIP3/Akt signaling, contributing to the regulation of cell viability and transformation by the PI3K/Akt pathway. Datta S R et al. (1999) *Genes Dev* 13:2905-27; Elstrom R L et al. (2004) *Cancer Res* 64:3892-9. Therefore, the possibility that PIT-1 may cause dysregulation of energy homeostasis and induction of the metabolic stress in cancer cells, which may contribute to the PIT-induced cell death, was investigated. Treatment with PIT-1 indeed induced significant increase in the phosphorylation of AMP-activated protein kinase (AMPK), a key factor in regulation of energy homeostasis activated by energy depletion. Hardie D G (2007) *Nat Rev Mol Cell Biol* 8:774-85. Increased phosphorylation of the main substrate of AMPK, acetyl-CoA carboxylase (ACC), consistently was also observed following treatment with PIT-1. The treatment of U87MG cells with PIT-1 prominently increased the expression of the autophagic marker LC3-II, which formed characteristic perinuclear punctate staining. This result is indicative of the induction of autophagy, a large-scale catabolic process playing a key role in cellular adaptation to metabolic stress. Mathew R et al. (2007) *Nat Rev Cancer* 7:961-7. Electron microscopy also showed the appearance of characteristic double membrane-enclosed autophagic vesicles even at the early stage of PIT-1 treatment. This result is indicative of the induction of autophagy, a large scale catabolic process playing a key role in mediating cellular adaptation to metabolic stress, consistent with the induction of metabolic stress by PIT-1. It is also consistent with the established role of Akt as an inhibitor of autophagy. This result is also consistent with the induction of the metabolic stress by PIT-1 and is reminiscent of previous reports showing enhancement of autophagy by Akt kinase inhibitors, e.g., in response to rapamycin treatment. Takeuchi H et al. (2005) *Cancer Res* 65:3336-46.

Since PITs were found to induce the hallmarks of metabolic stress, the possibility that PIT toxicity is enhanced under conditions when cells are further predisposed to such stress by nutrient deprivation was investigated. Indeed, a dramatic induction of cell death by the combination of glucose/glutamine deprivation and PIT-1 or PIT-2 (but not PIT-1i-1) treatment, which by far exceeded the toxicity of each of these stimuli separately, was observed. Moreover, it was found that Akt kinase inhibitor VIII synergized with inhibitors of mitochondrial respiration and ATP synthase (oligomycin, antimycin A, and rotenone) in inducing cell death, which is consistent with the role of Akt in promoting glycolysis. Elstrom R L et al. (2004) *Cancer Res* 64:3892-9. Similar result was also obtained using PIT-1. These data demonstrate that PITs indeed induce prominent metabolic stress, contributing to cell demise. Furthermore, the dramatic synergy between exogenous metabolic stress and PITs suggests that PITs may be expected to display increased cytotoxicity towards cancer cells in vivo as such cells are chronically subjected to exogenous metabolic stress conditions.

Example 5

PIT-1 and PIT-2 Inhibit Migration and Invasion of Cancer Cells

Multiple reports indicate that PIP3 is a key modulator of cell migration and growth factor-induced cytoskeleton remodeling, in addition to regulation of cell survival and metabolism. Cantley L C et al. (2002) *Science* 296:1655-7; Vivanco I et al. (2002) *Biochem J* 345 Pt 3:719-24. Loss of PTEN was found to dramatically increase motility of cancer cells and, conversely, re-expression of PTEN was found to markedly reduce invasiveness. Gildea J J et al. (2004) *Oncogene* 23:6788-97. Accordingly, the effect of PIT-1 on cell migration and invasion was investigated.

Two models of cell migration were used, a transwell migration model and a wound closure model. Migration of cancer and endothelial cells was evaluated using 24-transwell Boyden chamber (Costar, Bedford, Mass.) with a polystyrene membrane (6.5 mm diameter, 10 µm thickness, and 8 µm pore size). Cells were suspended in serum-free media and seeded in the upper compartment of each well ($2\times10^4$ cells/well) in the presence or absence of different compounds at the indicated concentrations. The lower compartment contained 600 µl of serum-free culture media supplemented with growth factors. After an 8-hr incubation at 37° C., cells were fixed and stained with 0.1% crystal violet. Non-migrating cells on the upper surface of the filter were removed, and the stained cells that migrated to the lower side were photographed using a phase-contrast microscope (Nikon, Japan) in five random fields. The cells were lysed with 10% acetic acid, and colorimetric determination was made at 595 nm using Wallac Victor 3 plate reader.

Cancer or endothelial cells were seeded into fibronectin-coated 96-well plates ($2\times10^4$ cells/well). After reaching confluence, cell monolayers were scratched with a pipette tip to obtain a "wound". The media and dislodged cells were aspirated and replaced by fresh serum-free media in the presence of growth factors, with or without compounds at different concentrations. After an 8-hr incubation at 37° C., cells were photographed using a phase-contrast microscope in five random fields. The width of wounded cell monolayers in images was measured and the inhibition rates of migration were calculated as inhibition rate=[1−(compound-treated group/control group)]×100%, and $IC_{50}$ value was determined using Origin6 software (MicroCal, LLC, Northampton, Mass.).

PIT-1 substantially inhibited growth factor-induced transwell migration of human cancer cells in a dose-dependent fashion. Similar inhibition of cell migration was observed using the wound healing assay. Consistent with the specific mode of inhibition, PIT-2 also efficiently inhibited cell migration, while neither PIT-1i-1 nor PIT-1i-2 was active. Notably, the inhibitory effect on cancer cell migration exerted by PIT-1 was much stronger than that of Akt kinase inhibitor VIII. This result is consistent with a well established role of PIP3 targets other than Akt in the regulation of cell migration, most notably PH domain-containing Rac/Rho GEFs (Fukata M et al. (2003) Curr Opin Cell Biol 15:590-7; Han J et al. (1998) Science 279:558-60; Hornstein I et al. (2004) Cell Signal 16:1-11), primarily regulating cell migration. This raised the possibility that inhibition of GEFs may contribute to the ability of PITs to suppress cell migration.

Both PIT-1 and PIT-2 (but not PIT-1i-1 and not PIT-1i-2) also efficiently suppressed cancer cell invasion through matrigel. Simpson K J et al. (2004) Cancer Res 64:8694-701. Importantly, PIT-1 treatment had no significant cytotoxic effects on the cells at the low concentrations used in the migration and invasion experiments (P>0.05), implying that the effect of PIT-1 on cell motility was not merely a consequence of cellular toxicity. Consistent with this result, treatment of the aggressive human breast carcinoma SUM-159 cells with PIT-1 blocked acquisition of the invasive phenotype by these cells. Notably, this effect was reversible, again indicating that it was not a mere consequence of cell death. Overall, these data show that PITs display multiple tumor-suppressive properties, potently inhibiting both cell viability and invasiveness, consistent with the role of the PIP3 signaling network in these events.

Example 6

PIT-1 and PIT-2 Inhibit Actin Polymerization, Cell Ruffling/Lamellipodia Formation, Cell Polarization, and Rac Activation Cell motility is driven by actin rearrangement and lamellipodia formation at the leading edge of the cell. Oikawa T et al. (2004) Nat Cell Biol 6:420-6. The PI3K pathway plays an important role in the regulation of these processes. von Philipsborn A et al. (2007) Int Rev Cytol 263:1-62. PIP3 affects this process at multiple levels, including that of the PDK1 and Akt (Stambolic V et al. (2006) Trends Cell Biol 16:461-6), PH-domain containing Rac/Rho family GEFs (VAV proteins, TRIO, PIX, etc.) (Hornstein I et al. (2004) Cell Signal 16:1-11), and WAVE-dependent actin polymerization Arp2/3 complex (Oikawa T et al. (2004) Nat Cell Biol 6:420-6). Therefore, considering efficient inhibition of cell migration by PITs, their effect on actin organization and membrane ruffling was examined.

In one set of experiments, the ability of PITs to inhibit actin polymerization and ruffling/lamellipodia formation was examined in SUM159 cells. Cells were serum starved and treated with PITs (25, 50 100 µM) or PIT-1 is (100 µM) for 8 hr, followed by PDGF (100 ng/ml) stimulation for 15 min. Cells were fixed and stained with TRITC-phalloidin to visualize actin fibers, followed by fluorescent microscopy analysis. The number of cells with ruffles/lamellipodia was counted in five random fields.

In another set of experiments, the ability of PITs to inhibit fMLP-stimulated HL-60 cell polarization was examined. Differentiated HL-60 cells were treated with PIT-1, PIT-2, PIT-1i-1, or PIT-1i-2, each at 100 µM for 2 hr, followed by stimulation with 100 nM fMLP for 3 min. Actin was stained and analyzed using fluorescent microscopy. The number of the polarized cells was counted in five random fields.

In order to measure cell polarization, wounds were generated in SUM159 cell monolayers, followed by serum starvation and treatment with 100 µM PIT-1, PIT-2, PIT-1i-1, or PIT-1i-2 for 2 hr. Cells were stimulated for 15 min with 100 ng/ml PDGF, fixed and stained with TRITC-phalloidin for F-actin (red), acetylated tubulin antibody (green) for microtubule organization center (MTOC), and Hoechst for nuclei (blue). Cell polarization was evaluated by analysis of the relative location of the MTOC and nucleus. A cell was considered polarized if MTOC was observed to the wound side of the nucleus. The number of polarized cells was counted in five random fields under fluorescent microscope.

It was found that membrane ruffling was prominently induced 15 minutes after PDGF stimulation of SUM159 cells. Ruffling was efficiently inhibited by pre-incubation with PIT-1 and PIT-2 (P<0.01), but not with PIT-1i-1 and PIT-1i-2, in a concentration-dependent manner. Furthermore, treatment with PITs significantly reduced the amount of F-actin in the cells, including both lamellipodia at the leading edge and stress fibers within cells, suggesting the effective inhibition of actin polymerization and remodeling.

Cells are dynamically polarized in response to extracellular signal gradients promoting directed cell migration (e.g., during chemotaxis and wound healing). To establish cell polarization, PIP3 accumulates at the leading edge and serves as a docking site for PH domain-containing proteins such as Rho/Rac family GEFs, leading to the rearrangement of actin cytoskeleton and formation of lamellipodia and filopodia at the front edge. Inhibition of PI3K has been previously found to inhibit cell polarization, e.g., during chemotaxis of neutrophils. von Philipsborn A et al. (2007) Int Rev Cytol 263:1-62; Wang F et al. (2002) Nat Cell Biol 4:513-8. In the wound healing model, both PIT-1 and PIT-2 were effective at preventing cell polarization and lamellipodia formation induced by PDGF stimulation (P<0.01), while both PIT-1i-1 and PIT-1i-2 failed to prevent cell polarization. Treatment with PIT-1 also resulted in the efficient inhibition of the fMLP-stimulated polarization of differentiated HL-60 neutrophils. These data indicate that inhibition of actin dynamics is a likely mechanism of inhibition of cell migration and invasiveness by PITs. It is also likely that this effect is exerted at multiple levels regulated by PIP3 as discussed above.

Of the PIP3-binding actin-regulating factors, VAV and WAVE family proteins have been identified as important PIP3-interacting proteins regulating actin polymerization, lamellipodia formation, and cell motility in response to growth factor stimulation. Hornstein I et al. (2004) Cell Signal 16:1-11; Oikawa T et al. (2004) Nat Cell Biol 6:420-6. Therefore, the effect of PIT-1 on the cellular localization of GFP fusions of VAV and WAVE proteins was investigated. SUM159 cells transfected with VAV2 or WAVE2 GFP vectors were treated with PIT-1, PIT-2, PIT-1i-1, or PIT-1i-2 (100 µM) for 2 hr. Alternatively, cells were serum starved overnight, treated with these same compounds and then stimulated with PDGF 100 ng/ml for 15 min. Subsequently, actin fibers were stained with TRITC-phalloidin and analyzed using fluorescent microscopy. The numbers of cell ruffles/lamellipodia were counted in five random fields.

Both VAV2- and WAVE2-transfected cells displayed a significantly increased number of peripheral lamellipodia/ruffles in the absence of PDGF stimulation. PITs efficiently abolished both lamellipodia formation and membrane translocation of these proteins. Both events were enhanced by PDGF and also suppressed by PITs. Similar results were also obtained using VAV3 and WAVE3 expression, while PIT-1i-1 and PIT-1i-2 were inactive.

It was also determined are PITs are capable of inhibiting cell migration in the presence of the overexpressed VAV and WAVE proteins. SUM159 cells were transfected with VAV2 or WAVE2. Scratch wound was generated in cell monolayer, followed by treatment with PIT-1 (100 µM) in the presence of PDGF (100 ng/ml) stimulation for 8 hr. The inhibitory effect of PITs on VAV- or WAVE-induced cell migration was calculated according to the width of wound. The width of wounded cell monolayers was measured in five random fields. Overexpression of VAV and WAVE proteins led to an increased cell migration in the wound healing model following stimulation with PDGF. Both PIT-1 and PIT-2 exhibited a larger degree of inhibition of cell migration in VAV- and WAVE-overexpressing cells compared to control cells, consistent with the contribution of these proteins to cell migration and inhibition of their membrane translocation by PITs. Again, inactive analogs PIT-1i-1 and PIT-1i-2 lacked activity in these experiments.

Rho/Rac family, especially Rac1, plays a critical role in actin polymerization, membrane ruffling/lamellipodia formation, and cell motility (Ridley A J et al. (1992) *Cell* 70:401-410) downstream of the GEFs, e.g., VAV family, and upstream of the WAVE family. The effect of PITs on Rac1 activation was therefore analyzed. SUM159 cells were seeded on 10 cm$^2$ plates and serum starved overnight, treated with different PIT compounds at a variety of concentrations for 2 hr, and then stimulated with 100 ng/ml PDGF for 15 min. Next, cells were rinsed once with PBS, and 1 ml lysis buffer (25 mM Tris-HCl, pH 7.5, 150 mM NaCl, 5 mM MgCl$_2$, 1% NP-40, 1 mM DTT, 5% glycerol, 1 µg/ml aprotinin, 1 µg/ml leupeptin and 1 mM PMSF) was added per plate. The cells were scraped and transferred to a microcentrifuge tube, vortexed briefly, and incubated on ice for 5 min, followed by a centrifugation at 16,000×g at 4° C. for 15 min. The supernatant was collected. A sample of the lysate was used to ensure equal protein concentration in the samples. Next, 700 µl lysate, 20 µl glutathione-sepharose beads, and 20 µg GST-human Pak1-PBD were mixed together, and the reaction mixture was incubated at 4° C. for 1 hr with gentle rocking. The beads were then washed three times with lysis buffer, and proteins were eluted by boiling beads in 50 µl of the 2×SDS sample buffer at 95-100° C. for 5 min. Samples were subjected to western blot analysis using anti-Rac1 mouse monoclonal antibody (1:1,000 dilution) (BD Biosciences).

Notably, both PIT-1 and PIT-2, but not PIT-1i-1 and PIT-1i-2, efficiently suppressed the activation of Rac1 caused by growth factor stimulation. This result is consistent with the regulation of the PIP3-dependent Rac1 activation by PITs, presenting another point of PIT action in the cells. Simultaneous inhibition of multiple steps of the pathway (PDK1/Akt, Rac GEFs, WAVE) explains efficient inhibition of cancer cell migration and invasion by PITs, in contrast to the lack thereof by Akt kinase inhibitor VIII.

Example 7

PIT-1 Inhibits Endothelial Cell Migration and Angiogenesis In Vitro

Endothelial cell migration plays a central role in tumor angiogenesis. Avraamides C J et al. (2008) *Nat Rev Cancer* 8:604-17. Therefore, considering efficient inhibition of cancer cell migration by PITs, the possibility that these molecules may possess additional anti-tumor modality suppressing migration of endothelial cells was examined. First, human umbilical vein endothelial cells (HUVEC) cells were serum starved overnight, and treated with different concentrations of PIT-1 (50, 100 and 200 µM) for 2 hr, followed by stimulation with 10 ng/ml bFGF for 15 min, and the PIP3-dependent phosphorylation events were evaluated by Western blotting. It was determined that PIT-1 is indeed capable of blocking PI3K/PDK1/Akt signaling pathway in HUVEC, similar to that in cancer cells.

Second, HUVEC were serum starved and treated with PITs (25, 50 100 µM) or PIT-1 is (100 µM) for 8 hr, followed by bFGF (10 ng/ml) stimulation for 15 min. Cells were fixed and stained with TRITC-phalloidin to visualize actin fibers, followed by fluorescent microscopy analysis. The number of cell ruffles/lamellipodia was counted in five random fields. PIT-1 and PIT-2, but not inactive analogs, efficiently blocked migration of HUVEC cells in both wound healing and transwell assays, associated with significant inhibition on actin polymerization and cell ruffling/lamellipodia formation in endothelial cells.

Based on these results, the ability of PIT-1 to attenuate angiogenesis in vitro using endothelial tube formation and aortic ring assays was also examined. The tube formation assay was performed in 96-well plates. Wells were pre-coated with 70 µl of the Matrigel basement membrane matrix (BD Biosciences) per well for 1 hr at 37° C. HUVEC were suspended in serum-free M199 medium and plated on Matrigel at a density of 2×10$^4$ cells per well. PIT-1 was added at indicated concentrations (3.125-100 µM). After an 8 hr incubation at 37° C., phase-contrast images of the endothelial tubes were obtained using a Nikon TE2000 microscope, and tube formation was assessed by counting the number of closed tubes in five random fields from each well.

For the aortic ring assay, aortas were isolated from 6-week old Sprague-Dawley rats and immediately transferred to a culture dish with serum-free medium. The fibroadipose tissue around the aortas was carefully removed and the aortas were cut into 1-mm long aortic ring fragments. After three consecutive washes in serum-free medium, the aortic rings were embedded into 70 µl Matrigel in 96-well plate and fed with 100 µl of serum-free M199 medium with or without PIT-1 at different concentrations (3.125-100 µM). The medium was replaced every 24 hr. Phase-contrast images were obtained on day 6, and the numbers of microvessel outgrowths per ring were counted.

Treatment with PIT-1 resulted in efficient inhibition of tube formation in a concentration-dependent manner with an IC$_{50}$ of 7.75 µM. This effect was also observed with PIT-2, but not with PIT-1i-1. No loss of cell viability was observed under the conditions of the experiments (P>0.05).

Microvessel growth from rat aorta sections is the result of a combination of endothelial cell proliferation, migration, and tube formation, and thus provides a close approximation of in vivo angiogenesis. For this experiment the rat aortic rings were embedded in matrigel and then were treated with PIT-1 (3.125-100 µM) for 6 days, followed by counting the number of microvessel outgrowths under microscope. Similar with tube formation assay, PIT-1 treatment remarkably suppressed microvessel outgrowth in aortic ring sprouting experiment with IC$_{50}$ of 4.58 µM. Overall, these data indicate that PIT-1 is capable of blocking migration of both cancer and endothelial cells, demonstrating that this molecule is capable of blocking both metastasis and tumor angiogenesis.

Example 8

DM-PIT-1 Exerts Similar In Vitro Effects as PIT-1 and PIT-2, With Increased Activity Upon establishing a multimodal inhibition of the PIP3 signaling network by PIT-1 in vitro, analysis of its anti-cancer activity in vivo was investigated. With this in mind, a series of analogs of PIT-1 were screened to identify a molecule with improved activity for further in vivo tests. One of the molecules tested, an analog containing two extra methyl groups and lacking chlorine, DM-PIT-1 (FIG. 2), did not show any qualitative differences from PIT-1 across the range of assays used to characterize PIT-1. Furthermore, it displayed increased activity in these assays compared to PIT-1, e.g., in inducing cell death in U87MG cells, inhibition of cell migration, and inhibition of PI3K-PDK1-Akt signaling. DM-PIT-1 was selected for further in vivo experiments described below.

Example 9

Preparation of DM-PIT-1-Loaded Micelles

Due to the limited aqueous solubility of PIT-1 and PIT-2, DM-PIT-1 was loaded into long-circulating polyethylene glycol-phosphoethanolamine (PEG-PE) mixed micelles (DM-PIT-1-M) to facilitate in vivo bioavailability of the molecule. This method has been reported to be efficient for in vivo targeting of cancer cells by other poorly soluble anti-cancer drugs, such as m-porphyrin, tamoxifen, and taxol. Gao Z et al. (2003) *J Drug Target* 11:87-92; Torchilin V P et al. (2003) *Proc Natl Acad Sci USA* 100:6039-44.

1,2-Disteratoyl-sn-glycero-3-phosphoethanolamine-N-[Methoxy(polyethylene-glycol)-2000] (PEG-PE) was supplied in chloroform (10 mg/ml) and stored at −80° C. A stock solution of DM-PIT-1 (0.5 mg/ml) was prepared by dissolving 20 mg DM-PIT-1 in 40 ml acetonitrile and stored at 4° C. Two milliliters of DM-PIT-1 from stock solution was added to 2.5 ml chloroform solution of PEG-PE. The organic solvents were removed by rotary evaporation to form a thin film of drug/micelle mixture. This film was further dried under high vacuum overnight to remove any remaining traces of solvent. To form micelles, the film was rehydrated in 10 mM HEPES buffer, pH 7.4 and sonicated for 5 min. The non-incorporated, precipitated DM-PIT-1 was removed by filtration through a 0.22 μm filter (Fisher Scientific, USA). The amount of DM-PIT-1 was determined by isocratic reverse-phase HPLC (Hitachi, Elite La Chrome) equipped with photodiode-array detector (L-2455). The chromatographic separation was performed on a C-18 column (5 μm, 4.6×250 mm, Hichrom, Calif.). Isocratic elution was performed with a mobile phase consisting of acetonitrile and water (70:30) containing 0.1% formic acid (v/v). The flow rate was 1 ml/min and the total run time was 10 min. Sample injection (10 or 20 μl) was performed with autosampler (Model L-2200, Hitachi). DM-PIT-1 was detected by the UV absorbance at 320 nm.

Drug content loading (%) was calculated as the weight of DM-PIT-1 in micelles divided by the PEG-PE weight which was used in micelle preparation.

The mean size of micellar preparations was measured by dynamic light scattering (DLS) with a scattering angle of 90° at 25° C. using a N4 Plus Submicron Particle System (Coulter Corporation, Miami, USA). The micelle suspensions were diluted with a 10 mM HB S, pH 7.4 until a concentration providing a light scattering intensity of $5\times10^4$ to $1\times10^6$ count was achieved. The measurements were done in triplicate.

The size of the DM-PIT-1-loaded micelles was about 15 nm with a narrow size distribution. The incorporation of DM-PIT-1 significantly increased the drug solubility (significant precipitation was observed with 300 μM of unencapsulated DM-PIT-1 in cell media, while no precipitate formed at 1 mM of DM-PIT-1-M in cell media). The DM-PIT-1-loaded micelles were stable in aqueous dispersions and did not appreciably change their size and size distribution or show any drug release for over one week (data not shown). Incorporation of DM-PIT-1 into micelles had no detrimental influence on induction of cell death by the molecule, nor on the synergy between DM-PIT-1 and TRAIL.

Example 10

PIT-1 and PIT-1 Analogs Inhibit In Vivo Tumor Growth

The effect of intravenous (i.v.) administration of both unencapsulated DM-PIT-1 in PBS and DM-PIT-1-M on the syngeneic 4T1 breast cancer growth in BALB/c mice was examined. 4T1 metastatic breast cancer cells were first cultured in vitro in DMEM medium containing 10% FBS and antibiotics. After re-suspension in PBS, the 4T1 cancer cells ($8\times10^4$) were injected s.c. into axillary regions of BALB/c mice. The treatment with PIT-1 began on day 11 after inoculation of tumor cells, i.e., when tumors were palpable, but before tumors are precisely measurable (~50 mm³). Working solutions of all PIT-1-formulations were made in sterile 0.9% NaCl before injection into mice. Free DM-PIT-1 and micellar DM-PIT-1 were administered i.v. daily at doses of 0.4 and 1 mg/kg, respectively, for 8 days. If the tumor size reached approx. 1000 mm³, the mice were euthanized using carbon dioxide ($CO_2$) prior to cervical dislocation. Seven mice per group were used. The tumor volume (V) was measured every two days by microcaliper for 8 days. Tumor volume was calculated according to the formula $(\alpha\times b^2)/2$, where α is the longest and b is the shortest diameter of tumor, respectively.

Tumor tissues were fixed in phosphate-buffered formalin, embedded in paraffin, cut in 4 μm thickness, and applied to slides. The slides were deparaffinized in xylenes using three changes for 5 min each, and hydrated gradually through graded alcohols: 100% ethanol twice for 10 min each, 95% ethanol twice for 10 min each, and then deionized water for 1 min with stirring. For antigen unmasking, slides were placed in a container, covered with 10 mM sodium citrate buffer, pH 6.0, and heated in a convection steamer for 1 hr. The slides were washed in deionized water three times for 2 min each, blocked with 5% normal goat blocking serum for 30 min, incubated with goat anti-CD31 primary antibody for 1 hr, and incubated with an Alexa Fluor 488-conjugated secondary antibody for 30 min. The slides were analyzed and photographed using a fluorescent microscope. TUNEL staining was performed using FragEL kit according to manufacturer's instructions (Calbiochem).

Figure 12:
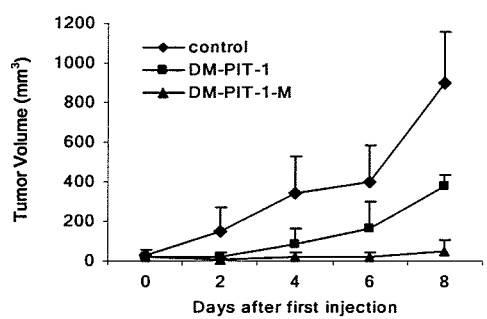
FIG. 12 is a bar graph depicting that administration of DM-PIT-1 or DM-PIT-1-M for 8 days attenuates syngeneic 4T1 breast tumor growth (volume) in BALB/c mice. After inoculation of tumor cells, DM-PIT-1 or DM-PIT-1-M were administered i.v. daily at doses of 0.4 mg/kg and 1 mg/kg, respectively, for 8 days. Tumor volumes as measured every two days are shown.

Administration of both DM-PIT-1 and DM-PIT-1-M significantly attenuated tumor growth in vivo compared to control after 8-day administration (P<0.01). Use of the micellar form of DM-PIT-1 (DM-PIT-1-M) made it possible to deliver a substantially higher dose (1 mg/kg/day) of the drug compared to the free drug (0.4 mg/kg/day) due to the increased solubility, leading to a more pronounced inhibition of tumor growth (P<0.01). In particular, on day 8 of the treatment, free DM-PIT-1 and DM-PIT-1-M reduced tumor volume by 58.1% and 95.2%, respectively, as compared to control (from 902.5±153 mm³ to 380±52.3 mm³ and 50±19.6 mm³) (FIG. 12). At the same time, administration of micellar DM-PIT-1 was well tolerated by healthy mice without any signs of overt toxicity or loss of weight.

Consistent with the cytotoxicity of PIT-1 in vitro, analysis of the tumors from the animals treated with DM-PIT-1M showed widespread induction of apoptosis measured using TUNEL assay. In addition, the nuclei of treated cells displayed characteristic nuclear fragmentation. Western blot results showed that treatment with DM-PIT-1M caused a significant increase in cleavage/activation of caspase-3, as well as cleavage of its substrate, PARP. Furthermore, consistent with the in vitro mechanism of action, the administration of DM-PIT-1M efficiently suppressed PI3K/PIP3 signaling in the tumor cells.

Example 11

PIT-1 and PIT-1 Analogs Inhibit In Vivo Tumor Angiogenesis

In view of the significant inhibitory effect of PIT-1 on angiogenesis observed in vitro, the extent of angiogenesis in DM-PIT-1-treated tumors was examined in vivo using microvasculature marker CD31. Administration of DM-PTI-1 resulted in the attenuation of a number of CD31 loci, reflecting marked decrease in cancer angiogenesis in vivo. Suppression of angiogenesis also likely contributed to the suppression of tumor growth by DM-PIT-1 treatment in vivo, considering a relatively low dose of the compound used in the experiments.

Example 12

PIT-1 and PIT-1 Analogs Inhibit In Vivo Tumor Metastasis

Since PIT-1 efficiently suppressed cell migration in vitro, the effect of DM-PIT-1-M on experimental pulmonary metastasis formation in vivo was also tested. B16-F10 melanoma cells were first cultured in vitro in DMEM medium containing 10% FBS and antibiotics. Then the cells were harvested and resuspended in 5 ml PBS, and cell viability was determined using trypan blue. Melanoma cells ($8 \times 10^4$) in 0.2 ml PBS were injected into the lateral tail vein of female C57BL/6 mice. A total of 21 mice were divided into three groups: control, plain micelles group, and micellar DM-PIT-1. The plain PEG-PE micelles were prepared using the same lipid component, and used at the same concentration as DM-PIT-1-loaded micelles. All micellar compositions were injected intraperitoneally (i.p.) at 0.2 ml/20 g body weight every 12 hr in daily injections of 5 mg/kg of DM-PIT-1. The drug treatment started 24 hr before melanoma cell injection and continued until the sixth day of the experiment. Body weights of mice were monitored three times a week, and the change in weight is expressed as % of control. Fourteen days after inoculation of melanoma cells, all mice were euthanized. Lungs were isolated, separated into individual lobes, and the number of surface metastatic foci was counted.

Administration of DM-PIT-1-M (5 mg/kg/day) resulted in a significant suppression on pulmonary metastasis formation by B16-F10 melanoma cells, injected through tail vein on the day 1. Drug administration for 5 days resulted in 55.3% reduction in the number of pulmonary metastasis, which were analyzed 18 days after melanoma cell injection. The mean number of metastatic colonies in animals administered micellar PIT-1 was 36.6, compared with 81.8 colonies in the control group. The reduction in metastasis was statistically significant ($P<0.01$) compared to both control and plain micelle groups (no statistically significant difference between control and plain micelles groups, $P>0.05$). Moreover, no significant loss in body weight after 5 day treatment ($P>0.05$) nor other signs of toxicity were observed, indicating that DM-PIT-1-M was well tolerated.

Example 13

PITs are Functionally Distinct From, and Act Synergistically With, Known Akt Inhibitors Comparison of PIT-1 with several previously reported inhibitors of Akt kinase activity showed differences in mechanism. U87MG cells were treated with 100 μM PIT-1, or 10 μM Akt inhibitor VIII (Calbiochem) or Akt inhibitor (Calbiochem), or 100 μM PIT-1 together with 10 μM Akt inhibitor VIII or Akt inhibitor, for 12 hr and then phosphorylation events were evaluated by western blot. In a separate experiment, U87MG cells were treated with 100 μM PIT-1 together with 10 μM Akt inhibitor VIII or Akt inhibitor for 24 hr and then cell viability was determined using ATP assay.

Neither Akt inhibitor X nor allosteric inhibitor VIII blocked membrane translocation of Akt PH domain. Furthermore, PIT-1 and the Akt kinase inhibitors acted synergistically in attenuating Akt activation, phosphorylation of downstream targets, and inhibition of cell survival. Conversely, no additive effect was observed when Akt inhibitors VIII and X were combined. These results emphasize that PITs represent a distinct class of Akt inhibitors and indicate that their mechanistic differences can be exploited to achieve efficient inhibition of Akt signaling by combining PH domain-targeting PITs with inhibitors of Akt kinase activity.

Example 14

Additional Molecular Modeling of Distinct PH Domains

Example 1 describes NMR analysis and molecular modeling of the PIT-1/Akt PH domain binding. Inositol-(1,3,4,5)-tetrakisphosphate-based overlay of three-dimensional crystal structures of PH domains of Akt, GRP1, and PDK1 revealed a non-conservative substitution of Leu52 (L52) in the PIP3-binding pocket of Akt by structurally equivalent Arg305 (R305) of GRP1 and Lys495 (K495) of PDK1. See, for example, GenBank Accession Nos. NP_004218 (human GRP1) (SEQ ID NO:2) and NP_002604 (human PDK1) (SEQ ID NO:3). These residues were modeled to be in proximity to the nitro group of PIT-1.

Example 15

Improved Activity and Modulation of Selectivity of PITs Toward PH Domains

Based on the results of Example 14, it was hypothesized that hydrophobic groups in positions $R^3$, $R^4$, and $R^5$ of Formula II would be preferred for Akt and disfavored for PDK1 and GRP1 binding. A number of PIT-1 derivatives were synthesized and then characterized in vitro: PIT-3, PIT-4, PIT-5, PIT-6, and PIT-7 (See Tables 1 and 2).

TABLE 1

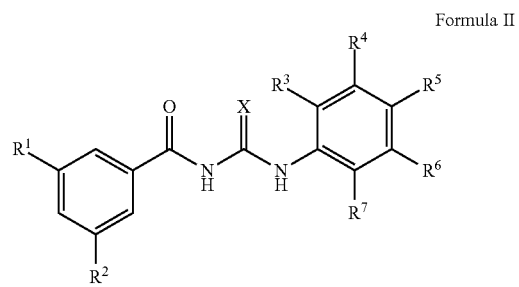

Formula II

Structures of Selected PITs

| Compound | $R^1$ | $R^2$ | $R^3$ | $R^4$ | $R^5$ | $R^6$ | $R^7$ | X |
|---|---|---|---|---|---|---|---|---|
| PIT-1 | H | H | H | $NO_2$ | H | Cl | OH | S |
| PIT-1i-1 | H | H | H | $NO_2$ | H | Cl | OH | O |
| PIT-1i-2 | H | H | H | $NO_2$ | H | Cl | OMe | S |
| DM-PIT-1 | Me | Me | H | $NO_2$ | H | H | H | S |
| PIT-3 | Me | Me | Me | Cl | Me | H | OH | S |
| PIT-4 | Me | Me | H | $CF_3$ | H | H | OH | S |
| PIT-5 | Me | Me | $CF_3$ | H | $CF_3$ | H | OH | S |
| PIT-6 | Me | Me | Me | Br | Me | H | OH | S |
| PIT-7 | Me | Me | H | Ph | H | H | OH | S |

Me = methyl; Ph = phenyl

Preparation of PIT-1 Derivatives

General:

Column chromatography was carried out by using Spectrochem silica gel (60-120, 230-400 mesh). $^1$H and $^{13}$C NMR spectroscopy measurements were carried out on Bruker AC 200 MHz, or Bruker DRX 400 MHz, and TMS was used as internal standard. $^1$H and $^{13}$C NMR chemical shifts are reported in ppm downfield from tetramethylsilane and coupling constants (J) are reported in hertz (Hz). The following abbreviations are used to designate signal multiplicity: s=singlet, d=doublet, t=triplet, q=quartet, m=multiplet, br=broad. Mass spectroscopy (ESI, API-QStar Pulsar) was carried out on a Finnigan MAT-1020 spectrometer. Elemental analysis data were obtained on a Thermo Finnigan Flash EA 1112 Series CHNS Analyzer.

Preparation of Isothiocyanate:

At 0° C., a solution of 3,5-dimethylbenzoic acid (5.0 g, 33.3 mmol) in dichloromethane (30 ml) was treated with oxalyl chloride (7.0 ml, 83.2 mmol) and the contents were stirred at room temperature for 8 hr. The reaction mixture was concentrated under reduced pressure and dried under high vacuum. The resulting crude acid chloride was added to a suspension of powdered ammonium thiocyanate (3.8 g, 50 mmol) and PEG-400 (100 mg) in methylene dichloride (25 ml) and stirred at room temperature for 3 hr. The reaction mixture was filtered and concentrated under reduced pressure. The crude acylisothiocyanate could be stored without any decomposition for more than a week at −20° C.

Preparation of Acylthiourea:

The above isothiocyanate (ca. 1 mmol) was dissolved in dichloromethane or/and acetonitrile (whenever the aminophenol was not soluble in DCM) (10 ml) and treated with amino phenol (1.8 mmol). The contents were stirred at room temperature until the reaction was completed (as tracked by thin layer chromatography (TLC)). The reaction mixture was washed with water, dried over anhydrous sodium sulfate, and concentrated under reduced pressure. The crude was recrystallized from appropriate solvents to get pure acylthioureas or purified by column chromatography, when the thiourea was an oil.

PIT-3:

N-(3-Chloro-6-hydroxy-2,4-dimethylphenylcarbamothioyl)-3,5-dimethylbenzamide. Yield 79%, yellow color solid. M. P.: 185-186° C. IR (Nujol) ν: 3322, 1681, 1528, 1460, 1377, 1296, 1164, 1051, 720 cm$^{-1}$. $^1$H NMR (CDCl$_3$, 200 MHz): δ 2.37 (s, 3H), 2.39 (s, 3H), 2.42 (s, 6H), 6.23 (br s, 1H), 6.89 (s, 1H), 7.30 (s, 1H), 7.50 (s, 2H), 9.22 (s, 1H), 12.32 (s, 1H). ppm. $^{13}$C NMR (CDCl$_3$, 50 MHz): δ 16.2 (q), 20.9 (q), 21.2 (q), 118.7 (d), 123.5 (s), 125.4 (d), 127.0 (s), 130.9 (s), 132.4 (s), 135.7 (d), 137.5 (s), 139.1 (s), 148.9 (s), 167.9 (s), 179.1(s) ppm. ESI-MS (m/z) 385.8 (35%, [M+Na]$^+$), 301.4 (100%). CHN Calcd. for C$_{18}$H$_{19}$ClN$_2$O$_2$S: C, 59.58; H, 5.28; N, 7.72. Found: C, 59.83; H, 5.22; N, 7.81.

PIT-4:

N-(2-Hydroxy-5-(trifluoromethyl)phenylcarbamothioyl)-3,5-dimethylbenzamide. Yield 87%, color less solid, M. P.: 208-209° C. IR (Nujol) ν: 3425, 3392, 1740, 1652, 1567, 1374, 1233, 1144 cm$^{-1}$. $^1$H NMR [CDCl$_3$-DMSO-D$_6$ (3:1) 200 MHz]: δ 2.40 (s, 6H), 7.08 (d, J=8.34 Hz, 1H), 7.26 (s, 1H), 7.30 (dd, J=2.3, 8.6 Hz, 1H), 7.61 (s, 2H), 9.15 (d, J=1.76, Hz, 1H), 10.47 (s, 6H) ppm. $^{13}$C NMR [CDCl$_3$-DMSO-D$_6$ (3:1) 200 MHz]: δ 20.2 (q, 2C), 114.2 (d), 118.9 (d, $^3J_{CF}$=3.7 Hz), 119.5 (s), 122.2 (d, $^3J_{CF}$=3.7 Hz), 125.0 (d, 2C), 125.6 (s), 126.2 (s), 130.9 (s), 133.9 (d), 137.3 (s, 2C), 150.8 (s, $^4J_{CF}$=1.1 Hz), 167.0 (s), 176.7 (s) ppm. ESI-MS (m/z): 391.3 (100%, [M+Na]$^+$), 369.4 (30%), 357.4 (10%). CHN Calcd. for C$_{17}$H$_{15}$F$_3$N$_2$O$_2$S: C, 55.43; H, 4.10; N, 7.60. Found: C, 55.38; H, 4.07; N, 7.56.

PIT-5:

N-(2-Hydroxy-4,6-bis(trifluoromethyl)phenylcarbamothioyl)-3,5-dimethylbenzamide. M. P.: 167-168° C. IR (Nujol) ν: 3388, 2853, 1680, 1604, 1459, 1376, 1279, 1214, 1127, 761 cm$^{-1}$. $^1$H NMR (CDCl$_3$, 400 MHz): δ 2.42 (s, 6H), 6.85 (s, 1H), 7.32 (s, 1H), 7.52 (s, 2H), 7.61 (s, 2H), 9.32 (br s, 1H), 12.84 (br s, 1H) ppm. $^{13}$C NMR (CDCl$_3$, 100 MHz), δ 21.1 (q, 2C), 116.1 (d, (d, $^3J_{CF}$=3.7 Hz), 121.1 (s), 121.5 (d, $^3J_{CF}$=3.7 Hz), 123.5 (s, $^2J_{CF}$=32.3 Hz), 125.5 (d, 2C), 126.7 (s), 127.4 (s, $^2J_{CF}$=30.1 Hz), 130.5 (s), 131.5 (s, $^2J_{CF}$=34.5 Hz), 136.1 (d), 139.3 (s, 2C), 152.6 (s), 167.9 (s), 179.3 (s) ppm. ESI-MS (m/z): 459.4 (8%, [M+Na]$^+$), 425.4 (100%). CHN Calcd. for C$_{18}$H$_{14}$F$_6$N$_2$O$_2$S: C, 49.54; H, 3.23; N, 6.42. Found: C, 49.69; H, 3.28; N, 6.19.

PIT-6:

N-(3-Bromo-6-hydroxy-2,4-dimethylphenylcarbamothioyl)-3,5-dimethylbenzamide. Yield 81%, pale yellow solid, M.P.: 164.5-166.0° C. IR (CHCl$_3$) ν: 3325, 1679, 1605, 1515, 1403, 1211, 1157, 1024 cm$^{-1}$. $^1$H NMR (CDCl$_3$, 200 MHz): δ 2.41 (s, 9H), 2.44 (s, 3H), 6.92 (s, 1H), 7.30 (s, 1H), 7.50 (s, 2H), 9.26 (s, 1H), 12.31 (s, 1H) ppm. $^{13}$C NMR (CDCl$_3$, 125 MHz): δ 19.5 (q), 21.2 (q), 24.1 (q), 119.2 (d), 123.6 (s), 125.4 (d, 2C), 131.0 (s), 134.0 (s), 135.9 (d), 139.3 (s), 139.7 (s), 149.6 (s), 167.9 (s), 178.7 (s) ppm. ESI-MS (m/z): 431.1 (4%, [M+Na]$^+$), 395.3 (20%), 277.3 (100%). CHN Calcd. for C$_{18}$H$_{19}$BrN$_2$O$_2$S: C, 53.08; H, 4.70; N, 6.88. Found: C, 53.41; H, 5.00; N, 6.61.

PIT-7:

N-(4-Hydroxybiphenyl-3-ylcarbamothioyl)-3,5-dimethylbenzamide. Yellow color gum, $^1$H NMR (CDCl$_3$, 200 MHz): δ 2.42 (s, 6H), 7.17 (d, J=8.5 Hz, 1H), 7.30 (s, 1H), 7.36-7.40 (m, 1H), 7.43-7.48 (m, 2H), 7.50-7.60 (m, 5H), 7.69 (d, J=2.3 Hz, 1H), 9.22 (br s, 1H), 12.76 (br s, 1H) ppm. ESI-MS (m/z): 399.5 (100%, [M+Na]$^+$). CHN Calcd. for C$_{22}$H$_{20}$N$_2$O$_2$S: C, 70.19; H, 5.35; N, 7.44. Found: C, 70.41; H, 5.58; N, 7.21.

In Vitro Characterization of PIT-1 Derivatives:

To measure inhibition of PIP3/Akt PH domain interaction by PIT-1 derivatives, 15 nM TMR-conjugated PIP3 were incubated with 5 M Akt PH domain in the presence or absence of PITs (6.25-200 μM) for 30 min, followed by FP measurement.

To measure inhibition of PIP3/PDK1 PH domain interaction by PIT-1 derivatives, 15 nM TMR-conjugated PIP3 were incubated with 100 nM PDK1 PH domain in the presence or absence of PITs (6.25-200 μM) for 30 min, followed by FP measurement.

To measure inhibition of PIP3/GRP1 PH domain interaction by PIT-1 derivatives, 15 nM TMR-conjugated PIP3 were incubated with 100 nM GRP1 PH domain in the presence or absence of PITs (6.25-200 μM) for 30 min, followed by FP measurement.

To measure induction of cell death by PIT-1 derivatives, U87MG cells were incubated with PITs (1.56-300 μM) for 48 hr. Cell viability was determined using ATP assay.

Results are shown in Table 2.

Figure 13:
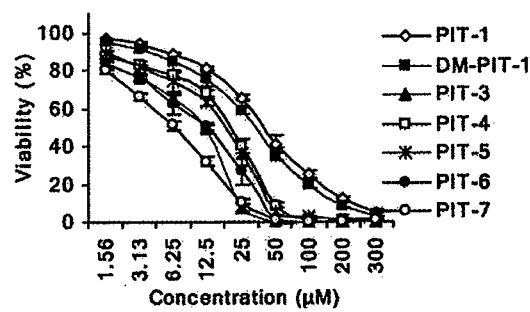
FIG. 13 is a graph depicting the induction of cell death by PIT-1 and derivatives of PIT-1. U87MG cells were incubated with indicated PITs (1.56-300 μM) for 48 hr. Cell viability was determined using ATP assay.
Figure 14:
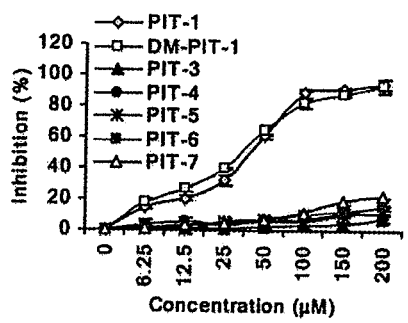
FIG. 14 is a graph depicting the inhibition of PIP/GRP1 PH domain interaction by PIT-1 and derivatives of PIT-1. PIP3 was incubated with 100 nM GRP1 PH domain in the presence or absence of indicated PITs (6.25-200 μM) for 30 min, followed by FP measurement.

PIT-3, PIT-4, PIT-5, and PIT-6 exhibited improved Akt potency and selectivity compared to PIT-1. Importantly, consistent with the proposed mechanism of cellular activity of PIT-1, increased affinity of PIT-1 derivatives towards Akt led to a substantially higher inhibition of Akt signaling in U87MG cells as well as increased cytotoxicity. See, for example, FIG. 13 and FIG. 14. Further, targeting of PDK1 may provide additional benefit, as PIT-7, displaying increased Akt binding and some PDK1 binding, exhibited the strongest activity in suppressing Akt signaling and reducing cancer cell viability. PIT-7 targeting PDK1 comparably to PIT-1 was unexpected, considering the lack of activity of some other PIT derivatives. It may be attributed to the ability of the phenyl group in R4 to form cation-pi interaction with charged sidechain of lysine 495 (K495) of PDK1. These interactions of PH domains can not be adequately assessed in the context of docked model and additional structural studies are used to refine the hypothesis.

TABLE 2

Activities of Selected PITs

| Compound | FP-Akt IC$_{50}$, μM | FP-PDK1 IC$_{50}$, μM | FP-GRP1 IC$_{50}$, μM | Cell Viability IC$_{50}$, μM |
|---|---|---|---|---|
| PIT-1 | 31.0 ± 02.5 | 66.7 ± 3.5 | 40.3 ± 2.8 | 39.9 ± 3.2 |
| PIT-1i-1 | — | — | — | — |
| PIT-1i-2 | — | — | — | — |
| DM-PIT-1 | 27.1 ± 3.2 | 80.5 ± 3.1 | 35.5 ± 3.8 | 33.9 ± 2.2 |
| PIT-3 | 17.5 ± 1.6 | 106.8 ± 3.9 | — | 12.4 ± 0.9 |
| PIT-4 | 22.6 ± 3.0 | — | — | 20.7 ± 3.3 |
| PIT-5 | 20.8 ± 2.5 | — | — | 18.8 ± 1.7 |
| PIT-6 | 18.1 ± 3.1 | — | — | 12.6 ± 2.1 |
| PIT-7 | 13.4 ± 2.1 | 52.3 ± 2.3 | — | 6.6 ± 0.3 |

"—" indicates >200 μM

Toxicity of new PIT-1 derivatives was significantly (P<0.05) attenuated by overexpression of PH domain-deficient activated Akt, consistent with the contribution of PITs/Akt PH domain interaction to cell death. In addition, all of the new PIT-1 derivatives remained inactive towards PIP3/Btk PH and PIP2/PLC-8/TAPP1/TAPP2 PH domain interactions. Overall, these data suggest that rational approach can be used for selective targeting PH domains. Specifically, activity of PIT-1 towards Akt and induction of cell death can be significantly increased by targeted chemotype modifications coupled with elimination of features that can present metabolic liabilities.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A pharmaceutical composition, comprising a therapeutically effective amount of a compound of Formula II

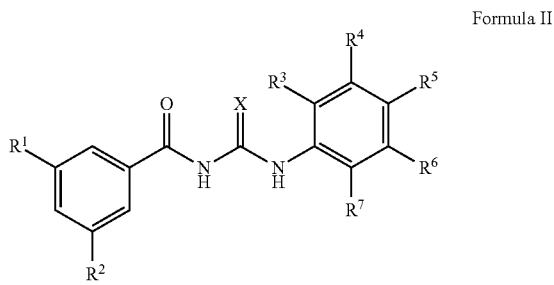

Formula II wherein
$R^1$ and $R^2$ are independently selected from H and —CH$_3$,
$R^3$ and $R^5$ are independently selected from H, —CH$_3$, and —CF$_3$,
$R^4$ is phenyl,
$R^6$ is H,
$R^7$ is OH, and
X is S;
and a water-soluble delivery vehicle.

2. A pharmaceutical composition, comprising a therapeutically effective amount of a compound of Formula II Formula II wherein
$R^1$ and $R^2$ are each —CH$_3$,
$R^3$ and $R^5$ are each H,
$R^4$ is —CF$_3$,
$R^6$ is H,
$R^7$ is OH, and
X is S;
and a water-soluble delivery vehicle.

3. A pharmaceutical composition, comprising a therapeutically effective amount of a compound of Formula II Formula II wherein
$R^1$ and $R^2$ are each —CH$_3$,
$R^3$ and $R^5$ are each —CF$_3$,
$R^4$ is H,
$R^6$ is H,
$R^7$ is OH, and
X is S,
and a water-soluble delivery vehicle.

4. A pharmaceutical composition, comprising a therapeutically effective amount of a compound of Formula II Formula II wherein
$R^1$ and $R^2$ are each —CH$_3$,
$R^3$ and $R^5$ are each H,
$R^4$ is phenyl,
$R^6$ is H,
$R^7$ is OH, and
X is S,
and a water-soluble delivery vehicle.

5. The pharmaceutical composition of any one of claims 1 and 2-4, wherein the composition is formulated as nanoparticles.

6. The pharmaceutical composition of claim 2, wherein the nanoparticles comprise polyethylene glycol-phosphoethanolamine (PEG-PE) micelles.

7. The pharmaceutical composition of any one of claims 1 and 2-4, wherein the water-soluble delivery vehicle comprises a targeting agent.

8. A compound of Formula II or a pharmaceutically acceptable salt thereof

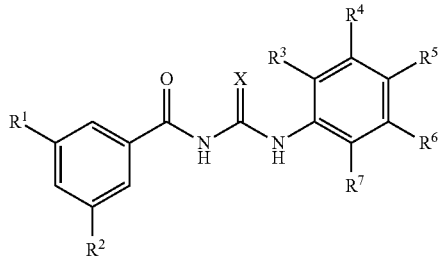

Formula II wherein
$R^1$ and $R^2$ are independently selected from H and —$CH_3$,
$R^3$ and $R^5$ are independently selected from H, —$CH_3$, and —$CF_3$,
$R^4$ is phenyl,
$R^6$ is H,
$R^7$ is OH, and
X is S.

9. A compound of Formula II or a pharmaceutically acceptable salt thereof

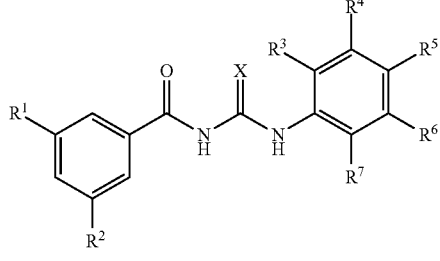

Formula II wherein
$R^1$ and $R^2$ are each —$CH_3$,
$R^3$ and $R^5$ are each H,
$R^4$ is —$CF_3$,
$R^6$ is H,
$R^7$ is OH, and
X is S.

10. A compound of Formula II or a pharmaceutically acceptable salt thereof

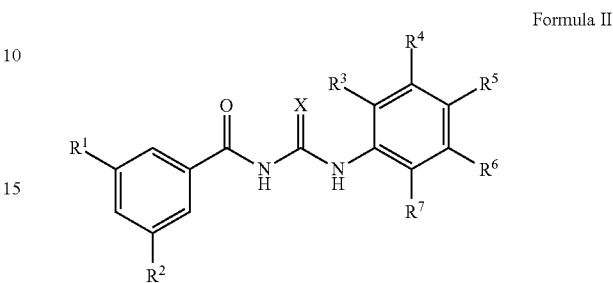

Formula II wherein
$R^1$ and $R^2$ are each —$CH_3$,
$R^3$ and $R^5$ are each —$CF_3$,
$R^4$ is H,
$R^6$ is H,
$R^7$ is OH, and
X is S.

11. A compound of Formula II or a pharmaceutically acceptable salt thereof

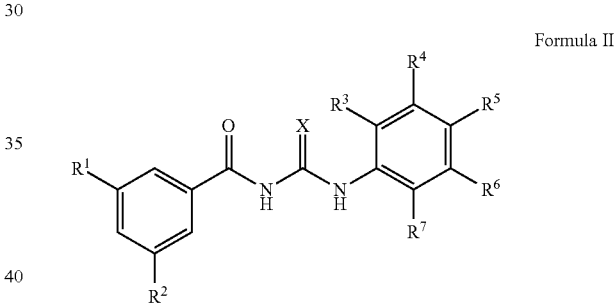

Formula II wherein
$R^1$ and $R^2$ are each —$CH_3$,
$R^3$ and $R^5$ are each H,
$R^4$ is phenyl,
$R^6$ is H,
$R^7$ is OH, and
X is S.

* * * * *

UNITED STATES PATENT AND TRADEMARK OFFICE
CERTIFICATE OF CORRECTION

| | | |
|---|---|---|
| PATENT NO. | : 8,628,961 B2 | Page 1 of 1 |
| APPLICATION NO. | : 13/109513 | |
| DATED | : January 14, 2014 | |
| INVENTOR(S) | : Alexei Degterev et al. | |

It is certified that error appears in the above-identified patent and that said Letters Patent is hereby corrected as shown below:

In the Claims:

At column 49, line 4, replace

"The pharmaceutical composition of claim 2,"

with

-- The pharmaceutical composition of claim 5, --.

Signed and Sealed this
Twenty-second Day of April, 2014

Michelle K. Lee
*Deputy Director of the United States Patent and Trademark Office*